(12) United States Patent
Jenkins et al.

(10) Patent No.: US 9,341,603 B1
(45) Date of Patent: May 17, 2016

(54) HANDHELD ULTRASOUND DETECTION APPARATUS HAVING A FLEXIBLE TUBE

(71) Applicants: John Jenkins, Nashville, TN (US);
Howard Sampson, Nashville, TN (US);
Michael Stumpf, Nashville, TN (US);
Myles Izikoff, Hendersonville, TN (US)

(72) Inventors: John Jenkins, Nashville, TN (US);
Howard Sampson, Nashville, TN (US);
Michael Stumpf, Nashville, TN (US);
Myles Izikoff, Hendersonville, TN (US)

(*) Notice: Subject to any disclaimer, the term of this patent is extended or adjusted under 35 U.S.C. 154(b) by 488 days.

(21) Appl. No.: 13/949,322

(22) Filed: Jul. 24, 2013

Related U.S. Application Data

(63) Continuation-in-part of application No. 12/847,629, filed on Jul. 30, 2010, now Pat. No. 8,495,914.

(60) Provisional application No. 61/273,065, filed on Jul. 30, 2009.

(51) Int. Cl.

| | | |
|---|---|---|
| *G01N 29/14* | (2006.01) | |
| *G01N 29/28* | (2006.01) | |
| *G01N 29/36* | (2006.01) | |
| *G01N 29/40* | (2006.01) | |
| *G01N 29/24* | (2006.01) | |
| *G01M 3/24* | (2006.01) | |
| *G01N 29/22* | (2006.01) | |

(52) U.S. Cl.
CPC ............ *G01N 29/36* (2013.01); *G01N 29/2456* (2013.01); *G01N 29/40* (2013.01); *G01N 29/221* (2013.01); *G01N 29/226* (2013.01)

(58) Field of Classification Search
CPC ..... G01N 29/36; G01N 29/221; G01N 29/226; G01N 29/24; G01N 29/2456; G01N 29/40; G01N 29/48
USPC ............... 73/601, 617, 642, 644, 587, 40.5 A
See application file for complete search history.

(56) References Cited

U.S. PATENT DOCUMENTS

| | | |
|---|---|---|
| 4,287,581 A | 9/1981 | Neale, Sr. |
| 4,987,769 A | 1/1991 | Peacock et al. |
| 5,445,026 A | 8/1995 | Eagan |
| 5,710,377 A | 1/1998 | Youngquist et al. |
| 5,854,422 A | 12/1998 | McKeon et al. |
| 5,955,670 A | 9/1999 | Goodman et al. |
| 6,057,959 A | 5/2000 | Taylor et al. |

(Continued)

*Primary Examiner* — Daniel S Larkin
*Assistant Examiner* — Rose M Miller
(74) *Attorney, Agent, or Firm* — Patterson Intellectual Property Law, P.C.; Lucian Wayne Beavers; Gary L. Montle

(57) ABSTRACT

A handheld ultrasound detection apparatus includes a portable housing with a flexible tube that extends from the housing and includes a sound cup and an ultrasound receiver for converting received ultrasound energy into an electronic signal. A gain/active filter includes four amplifiers each having an associated gain range. The apparatus is programmed based on a size of the electronic signal, to direct the electronic signal along a linear scale through one or more amplifiers and apply an appropriate gain to the signal, and to generate a percentage value corresponding to the gain and with respect to the linear scale. In a manual mode, data is generated corresponding to a particular gain range and a percentage value from 0-100% with respect to the particular gain range, while during an automatic mode data is generated corresponding to a percentage value from 0-400% with respect to a collective gain range.

17 Claims, 18 Drawing Sheets

(56) References Cited

U.S. PATENT DOCUMENTS

| | | | |
|---|---|---|---|
| 6,058,076 | A | 5/2000 | Komninos |
| 6,175,934 | B1 | 1/2001 | Hershey et al. |
| 6,220,098 | B1 | 4/2001 | Johnson et al. |
| 6,247,353 | B1 | 6/2001 | Battenberg et al. |
| 6,666,093 | B2 | 12/2003 | Morganti |
| 6,766,692 | B1 | 7/2004 | Eagan |
| 6,978,675 | B2 | 12/2005 | Eagan |
| 2005/0126264 | A1 | 6/2005 | Komninos |
| 2006/0053867 | A1 | 3/2006 | Stumpf |
| 2007/0109137 | A1 | 5/2007 | Farrel |
| 2007/0109138 | A1 | 5/2007 | Farrell |
| 2007/0112528 | A1 | 5/2007 | Farrell |
| 2010/0039271 | A1 | 2/2010 | Izikoff et al. |
| 2010/0097057 | A1 | 4/2010 | Karpen |

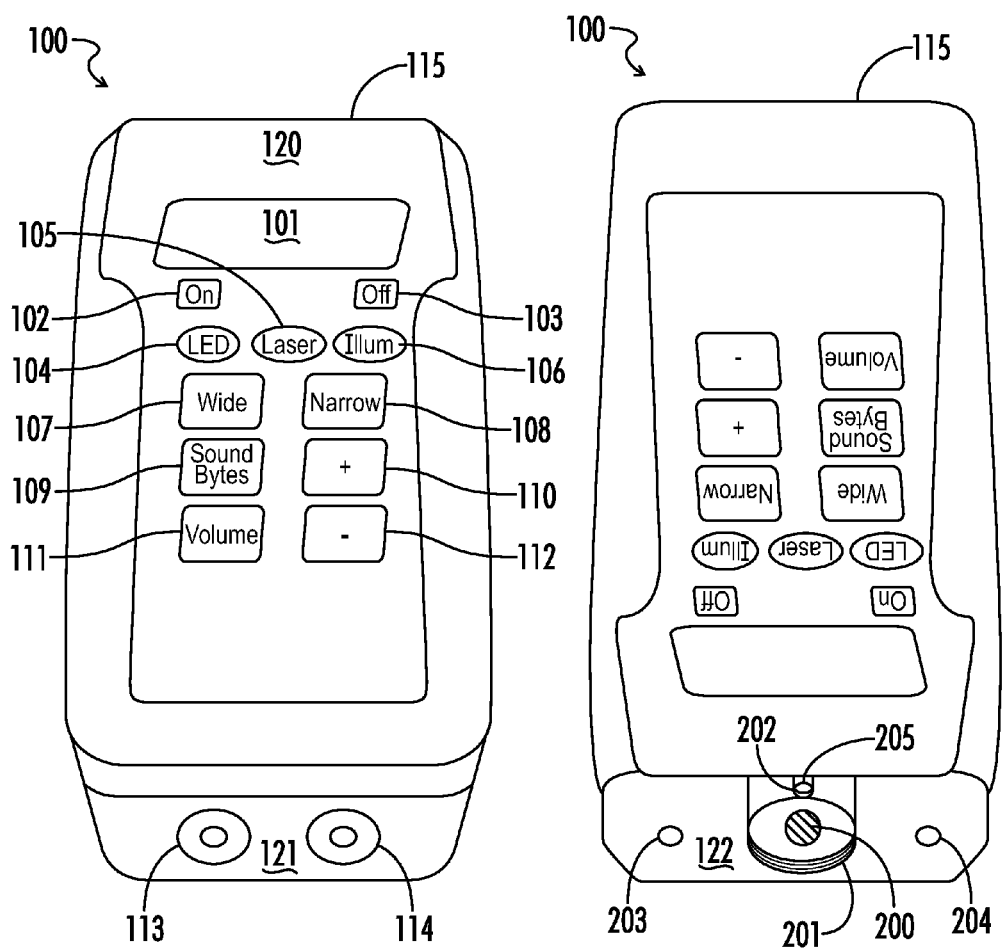

HANDHELD ULTRASOUND DETECTION APPARATUS HAVING A FLEXIBLE TUBE

CROSS-REFERENCES TO RELATED APPLICATIONS

This application is a continuation-in-part of U.S. patent application Ser. No. 12/847,629, and further claims the benefit of U.S. Provisional Application No. 61/273,065 filed on Jul. 30, 2009, the entire contents of which are herein incorporated by reference.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF THE INVENTION

The present invention relates generally to the field of utilizing ultrasound emissions for fault detection in industrial equipment. More particularly, the present invention relates to a system and method for locally collecting sound data from industrial equipment that may be used to determine the presence of faults and trends to failure that may be used as the basis for corrective action/preventative maintenance programs.

Briefly stated, ultrasound is acoustic energy in the form of sound waves. Ultrasound exhibits a frequency above the human hearing range. In this regard, the highest frequency that the human ear can detect is around twenty thousand Hertz (or 20,000 cycles per second).

BRIEF SUMMARY OF THE INVENTION

A handheld ultrasound detection apparatus in accordance with one embodiment as disclosed herein includes a portable housing with a flexible tube that extends from the housing and includes a sound cup and an ultrasound receiver for converting received ultrasound energy into an electronic signal. A gain/active filter includes four amplifiers each having an associated gain range. The apparatus is programmed based on a size of the electronic signal, to direct the electronic signal along a linear scale through one or more amplifiers and apply an appropriate gain to the signal, and to generate a percentage value corresponding to the gain and with respect to the linear scale.

In one particular aspect, the apparatus may enable user selection of a manual mode wherein data is generated corresponding to a particular gain range and a percentage value from 0-100% with respect to the particular gain range, or alternatively of an automatic mode wherein data is generated corresponding to a percentage value from 0-400% with respect to a collective gain range.

BRIEF DESCRIPTION OF THE SEVERAL VIEWS OF THE DRAWINGS

FIG. 1 is a back side perspective view of an exemplary handheld ultrasound detection apparatus in accordance with an embodiment of the present disclosure, showing the bottom of the apparatus.

FIG. 2 is a front side perspective view of the handheld ultrasound detection apparatus, such as is depicted in FIG. 1.

DETAILED DESCRIPTION OF THE INVENTION

Figure 3:
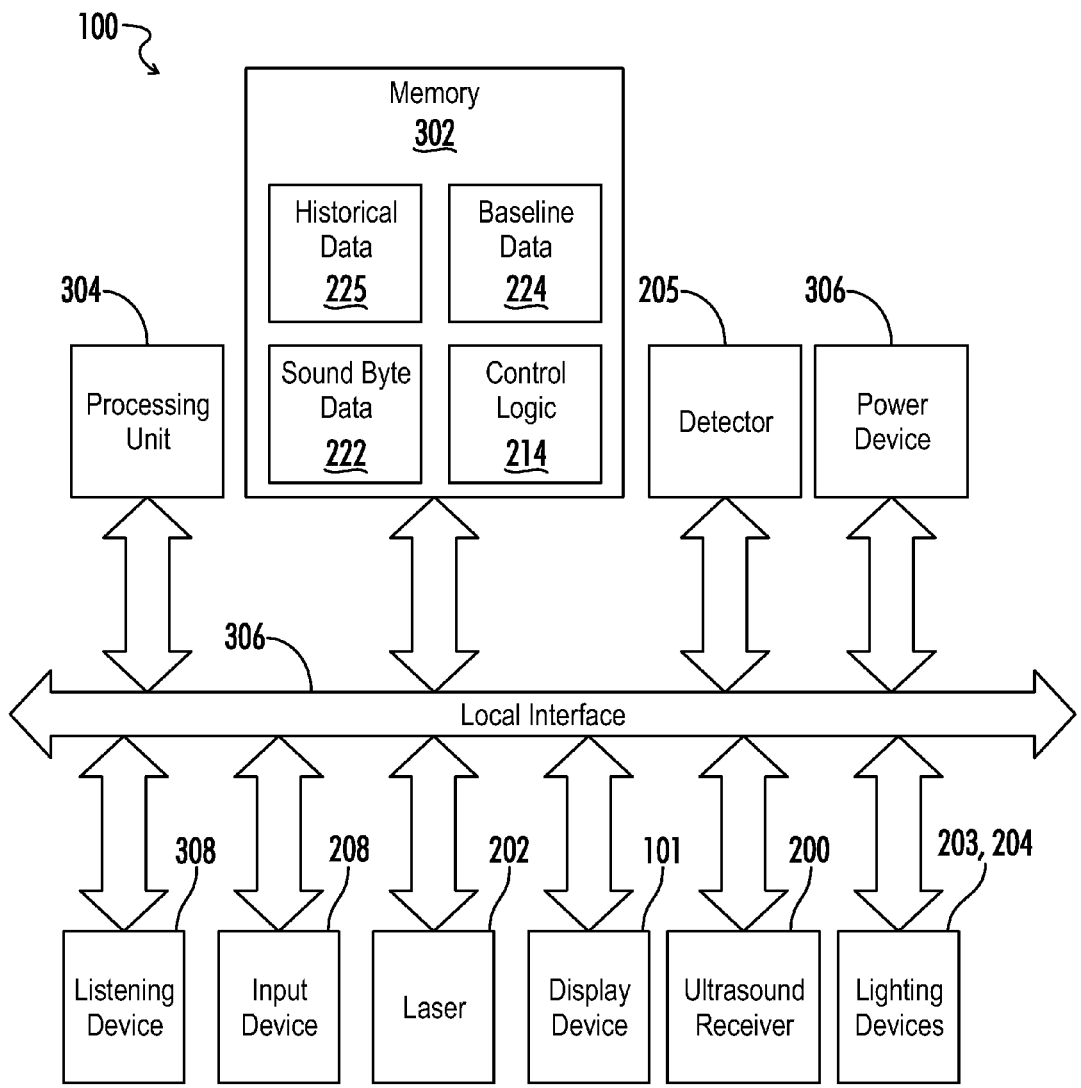
FIG. 3 is a block diagram depicting exemplary system components of the handheld ultrasound detection apparatus depicted in FIG. 1.

The present disclosure is best understood by referring to the drawings. The elements of the drawings are not necessarily to scale, emphasis instead being placed upon clearly illustrating the principles of the disclosure.

Oftentimes in particular environments, such as manufacturing environments, there are various incidents that may occur that the human ear cannot detect but that may be detectable by an ultrasound device. In this regard, leaks in pipes may emit ultrasound energy. In addition, electrical problems, for example corona discharge in an electrical box, may emit ultrasound energy that can be detected by an ultrasound device.

Thus, problems may be realized and averted by detection of ultrasound being emitted in a variety of situations. For example, a small leak in a pipe may not be detectable through use of the human ear, but by detection of ultrasound being emitted by the leak the leaky pipe can be addressed prior to the eventuality of a major leak. As another example, an electrical box may be experiencing problems that are undetectable by the human ear or by sight by detection of the ultrasound energy that is escaping when the corona discharge occurs. Thus, the electrical problem can be addressed prior to the eventuality of a major electrical outage.

The present disclosure relates to a handheld ultrasound detection apparatus that can be used in environments, such as manufacturing environments, for detecting ultrasound energy that is undetectable by the human ear. The handheld ultrasound detection apparatus can be used in wide mode, where a wide range of ultrasound energy is detectable, or the handheld ultrasound detection apparatus can be used in narrow mode for pinpointing the exact location of the source of ultrasound emissions without consequence related to any ultrasound energy that can be considered "noise."

The handheld ultrasound detection apparatus comprises a display device. The display device is for communicating to a user of the handheld ultrasound detection apparatus of characteristics of the ultrasound energy that is detected by the handheld ultrasound apparatus.

Further, the handheld ultrasound detection apparatus comprises a flexible tube that attaches onto the housing of the handheld ultrasound detection apparatus. The flexible tube allows the user to maneuver around corners, beams, pipes, or the like, to better obtain an ultrasound reading of a potential source of ultrasound energy.

FIG. 1 is a front side perspective view of a handheld ultrasound detection apparatus 100 in accordance with an embodiment of the present disclosure. The handheld ultrasound detection apparatus 100 comprises a housing 115 that houses electronic components described further herein with reference to FIG. 3.

The handheld ultrasound detection apparatus 100 further comprises a front side 120 comprising a display device 101, which can be, for example, a light emitting diode (LED) display device or a liquid crystal display (LCD) device. During operation, the display device 101 displays information relative to operation of the handheld ultrasound detection apparatus 100.

The handheld ultrasound detection apparatus 100 further comprises a plurality of control buttons 102-112. In particular, the handheld ultrasound detection apparatus 100 comprises an "On" button 102 and an "Off" button 103 for activating and deactivating the handheld ultrasound detection apparatus 100. In addition, the handheld ultrasound detection apparatus 100 further comprises an "LED" button 104 for activating the display device 101, a "Laser" button 105 and an "Illum" button 106, which are described further with reference to FIG. 2.

The handheld ultrasound detection apparatus 100 also comprises a "Wide" button 107 that when selected relatively increases the listening area of the handheld ultrasound detection apparatus 100. In addition, the handheld ultrasound detection apparatus 100 comprises a "Narrow" button 108 that when selected decreases the listening area of the handheld ultrasound detection apparatus 100. Actuating the Wide button 107 causes the apparatus to operate in the normal field of reception and is generally in the 40K hertz spectrum. When the Narrow field button 108 is selected, the apparatus 100 narrows the field of reception which reduces or eliminates competing noise. In this regard, a user (not shown) may use the apparatus 100 with the Wide button 107 actuated to narrow in on a potential leak location, and then select the Narrow button 108 to narrow the field and amplify the signal.

In one embodiment of the apparatus 100, the Narrow mode setting narrows the reception spectrum down to around 38.4 kilohertz (kHZ), plus or minus 1 kHz. In this regard, the apparatus 100 contains an 8-pole filter (not shown), that narrows the spectrum accordingly. When the apparatus 100 is in Wide mode, the 8-pole filter is bypassed so that a receiver 200 (FIG. 2) in the apparatus 100 receives all of the signals that the receiver 200 in the apparatus is capable of receiving. The receiver 200 generally receives signals at 40 kilohertz, plus or minus 2 kilohertz; therefore a wider range of signals is received when the apparatus 100 is in Wide mode.

Note that while the central frequency of 38.4 kHz+/−1 kHz is described as the reception spectrum when the handheld ultrasound detection apparatus is in narrow mode, other central frequencies and band sizes are possible in other embodiments. Further note that while the central frequency of 40 kHz+/−2 kHz is described as the reception spectrum when the handheld ultrasound detection apparatus is in wide mode, other central frequencies and band sizes are possible in other embodiments. See, e.g., FIGS. 19-22 for graphical representations of frequency (in kHz) versus magnitude (in dBm) for certain exemplary applications within the scope of the present disclosure.

The display device 101 displays the current field setting (i.e., Wide or Narrow). The display device 101 further displays signal intensity bars (not shown) that graphically reflect the intensity of the signal being received. Other types of field setting can possibly be displayed to the display device in other embodiments of the present disclosure.

The handheld ultrasound detection apparatus 100 further comprises a back end 121 comprising a plurality of ports 113 and 114 for receiving one or more listening devices (not shown). For example, headphones or earphones may be connected to the ports 113 and 114. A user holding the apparatus 100 can then hear sounds received and/or generated by the apparatus 100, which is described further herein.

The apparatus 100 further comprises a "Sound Bytes" button 109. In one embodiment, when the "Sound Bytes" button 109 is selected, the apparatus 100 transmits training sounds to the ports 113 and 114 for hearing by a user using the listening devices. In this regard, the apparatus 100 may display a list of sounds available for hearing that includes, for example, sounds of corona discharge or sounds of an air leak. Using a "+" button 110 and a "−" button 112, the user can scroll through the list of available sounds and select a sound from the list that the user desires to hear. Upon selection, the apparatus 100 generates sound indicative of, for example, a corona discharge or an air leak, and plays the sound for the user via the listening devices connected to the ports 113 and 114. The "Volume" button 111 can be used to increase and/or decrease the volume at which the user hears generated sounds.

FIG. 2 is a front end perspective view of the handheld ultrasound detection apparatus 100 showing a front end 122 of the apparatus 100. Notably, the front end 122 comprises the ultrasound receiver 200 embedded within a threaded cylindrical structure 201. The structure 201 is threaded for receiving receiver heads (not shown) that enable directed use of the receiver 200, and the implements are described further herein with reference to FIG. 5. In one embodiment, the receiver 200 is recessed within the structure 201; however, the receiver 200 may be located differently in other embodiments of the apparatus 100.

The handheld ultrasound detection apparatus 100 further comprises a laser 202 and a plurality of lighting devices 203 and 204, which can be light emitting diodes (LED), for example. During operation, the user can select the "Illum" button 106, which activates the lighting devices 203 and 204. Therefore, when the apparatus 100 is being used in a dimly lit environment, e.g., in an electrical panel when determining corona discharge, the lighting devices 203 and 204 illuminate the field of view.

When the "Laser" button 105 is activated, the laser 202 emits a laser beam pulse in a direction in which the front end 122 of the apparatus 100 is being pointed. In this regard, the laser beam pulse is emitted from the laser 202 in the same direction in which the front end 122 of the ultrasound receiver 200 is directed. Thus, the beam (not shown) emitted from the laser 202 falls approximately on an object (not shown) in the direction in which the receiver 202 is listening. Therefore, the laser 202 approximately "points" to the object that is being listened to by the receiver 202.

The apparatus further comprises a detector 205. The detector 205 receives light from the laser 202 that is reflected off an object at which the laser 202 is pointing. Such reflected light can be used to determine, based upon the distance traveled by light emitted from the laser 202, the distance of an object from the apparatus 100. This distance can be displayed to the display device 101.

In another embodiment, the detector 205 is an infrared sensor. In such an embodiment, the detector 205 may be used to determine the temperature of an object that is being pointed to by the laser 202.

FIG. 3 is a block diagram of an exemplary apparatus 100 of the present disclosure. The exemplary apparatus 100 generally comprises the ultrasound receiver 200, the lighting devices 203 and 204, and the display device 101, as described hereinabove with reference to FIGS. 1 and 2. In addition, the apparatus 100 further comprises a processing unit 304, a listening device 308, an input device 208, a detector 205, a laser 202, and a power device 306 all communicating over a local interface 306.

In one embodiment, the input device 208 comprises a keypad having the plurality of buttons 102-112 (FIGS. 1 and 2). Other input devices 208 are possible in other embodiments.

In one embodiment, the listening device 208 comprises at least one headphone and/or earphone, which connect to the ports 113 and 114 (FIG. 1). Other listening devices 208 are possible in other embodiments. For example, the apparatus 100 may further comprise a radio transmitter that wirelessly transmits data to wireless receivers worn by a user (not shown).

The apparatus 100 further comprises a power device 306 for providing electrical power to other components of the handheld ultrasound detection apparatus 100. The power device 306 may be, for example, a rechargeable battery pack that powers the components of the handheld ultrasound detection apparatus 100.

The apparatus 100 further comprises control logic 214. The control logic 214 can be software, hardware, or a combination thereof. In the exemplary apparatus 100, the control logic 214 is shown as software stored in memory 302. The memory 302 may be of any suitable type of computer memory known in the art, such as RAM, ROM, flash-type, and the like.

As noted herein, the control logic 214 is shown in FIG. 3 as software stored in memory 302. When stored in memory 302, the control logic 214 can be stored and transported on any computer-readable medium for use by or in connection with an instruction execution system that can fetch and execute the instructions. In the context of this document, a "computer-readable medium" can be any means that can contain or store the program for use by or in connection with an instruction execution apparatus. The computer readable medium can be, for example but not limited to, an electronic, magnetic, optical, electromagnetic, infrared, or semiconductor device. In alternative embodiments, as described further below, any or more of the control logic 214, memory 302, power device 306, or other components may reside in a separate housing that is electrically coupled to the first housing 115 and may for example be configured to be carried or worn in a hands-free manner by a user.

The processing unit 304 may be a digital processor or other type of circuitry configured to run the control logic 214 by processing and executing the instructions of the control logic 214. The processing unit 304 communicates to and drives the other elements within the apparatus 100 via the local interface 306, which can include one or more buses.

During operation, the user activates the apparatus 100 via the input device 208, which can comprise any of the plurality of buttons 102-112 (FIGS. 1 and 2). Upon activation, the control logic 214 calibrates the receiver 202 based upon baseline data 224 stored in memory 302. When the user activates the "Wide" button 107, the control logic 214 listens, via the receiver 202, for ultrasound signals in the 40K Hertz signal band within a tolerance of +/−2 kHz.

The control logic 214 displays to the display device 101 data indicating the percentage of saturation of the electronics with a sound signal received by the receiver 202. When the user selects the "Narrow" button 108, the control logic 214 listens, via the receiver 202, for ultrasound signals in the 38.4 kHz signal band within a tolerance of +/−1 kHz.

The control logic 214 then applies a gain to the signals such that the signals are then within an audible range of around 20 kHz. Thus, the signals being received via the receiver 202 are transmitted to the listening device 208 so that the user can recognize whether there is a recognizable sound, e.g., a corona discharge or an air leak.

When the user activates the "Sound Byte" button 109 (FIG. 1), the control logic 214 displays a list of identifiers identifying sound byte data 222 stored in memory 302. As an example, the sound byte data 222 may be a plurality of .wav files indicative of pre-recorded sounds common, for example, in an automotive plant. The user can select to hear one of the sounds, e.g., the stored sound of a corona discharge, via the input device 208. The control logic 214 plays the selected sound for the user via the listening device 308.

The control logic 214 may further store historical data 225 indicative of particular tests that have been performed on an identified object. For example, the data 225 may indicate that a test has been performed on a pipe identified as "Pipe 1." The historical data 225 can store the identifier Pipe 1 associated with an ultrasound reading taken from the receiver 202 and data indicative of how far away the reading was taken. Thereafter, the user can return to the same Pipe 1 and, based upon the previously generated data, take another reading at the same distance to determine if a detected leak has increased or changed.

As another example, the apparatus 100 may be used to capture sound and temperature data (not shown) related to a particular bearing. In this regard, the user may obtain data indicative of a sound reading from the receiver 202 and a temperature reading from the detector 205. This data may be stored as historical data 225. In the future, the user can recall the historical data 225 and compare it with a new sound reading and temperature reading to determine if the bearing has degenerated.

Further, the control logic 214 controls the emission of light from the laser 202 when the "Laser" button 105 (FIG. 1) is selected. In this regard, the control logic 214 initiates a laser light pulse from the laser 202. The light pulse emitted from the laser 202 travels to an object and is reflected off the object at which the apparatus 100 is pointed. The detector 205 receives the reflected light pulse, and the control logic 214 determines the distance from the apparatus 100 to the object by measuring the time delay between transmission of the light pulse and detection of the reflected signal.

Additionally, the control logic 214 further initiates and controls the calibration of the apparatus 100. In operation, the apparatus 100 calibrates itself based upon the signal received by the receiver 200 (FIG. 2). In this regard, when the apparatus first boots up, the calibration routine goes through each of four gain ranges bypassing the receiver and collects information about the direct current (DC) in each gain range. In this process, the "noise floor" in each gain range is obtained and recorded when no ultrasound energy is being received by the receiver 200, i.e., the receiver is deactivated. Such noise is that noise produced by the electronics in the device alone regardless of any ultrasound energy that may be being detected by the receiver, i.e., upon calibration the receiver is bypassed. After the calibration sequence is complete, the receiver 200 is put back online and the noise floor values are subtracted out for each range when ultrasound waves are received by the receiver 200.

The highest gain range employs the use of a high gain circuit that amplifies the output signal of the receiver 200. In one embodiment, the input signal is amplified 40,000 times, but other amounts of amplification are possible in other embodiments. Signals received on the low end of the ultrasound spectrum are as small as 0.3 micro volts ($\mu V$) and thus require high amplification in order to be able to translate the signal into the audible range. When this high gain is used in circuits, the circuits tend to drift with temperature and time and the like. When the gain is very high, even small deviations in temperature can result in a large offset in the circuitry. Signals may be varied by as much as a million to one on the high end, and this much gain would likely saturate all of the electronics. Therefore, the signal is attenuated automatically based upon its size. For example, if the incoming signal is too big for a gain range, the signal is automatically attenuated until the signal is just large enough so that it is in a linear range. If it is too small, gain is added automatically and the signal is raised up as far as possible without over-ranging. In other words, the amplification of the signal is controlled such that the output is in a predefined range.

In this regard, control logic 214 directs a signal through the appropriate amplifiers based upon the size of the signal. The signal is maintained into a linear range of the amplifiers to avoid introducing harmonics into the signal.

Figure 4:
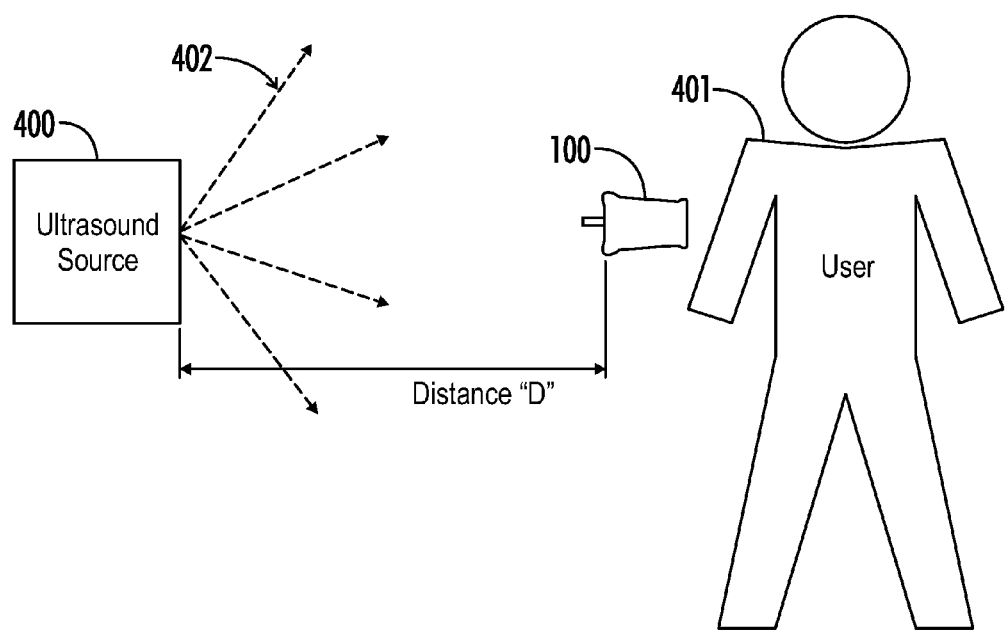
FIG. 4 depicts an exemplary use of the handheld ultrasound detection apparatus depicted in FIG. 1.

FIG. 4 depicts use of the apparatus 100, for example in the field of maintenance. Notably, a user 401, e.g., a maintenance technician, may desire to determine if there is a leak in the vicinity of the user 401. The user 401 activates the handheld ultrasound detection apparatus 100 via the "On" button 102 (FIG. 1).

Upon activation, the receiver 202 (FIG. 2) begins receiving data indicative of ultrasound from the vicinity. Thus, there can be a sound source 400 within the vicinity of the user 401 emitting ultrasound signals 402. The sound source 400 can be, for example, a transmitter that has been placed within a closed container to enable detection of leaks in the container. In addition, the sound source 400 can be a leaking pipe or an electrical box wherein a connection is experiencing corona discharge.

The detector 205 (FIG. 2) in the apparatus 100 can determine the distance "D" between the ultrasound source 400 and the user 401 by receiving light reflected off an object from the laser 202 (FIG. 2). The detector 205 receives reflected light from the laser 202. The distance "D" is displayed via the display device 101 (FIG. 1).

Based upon data displayed by the display device 101 (FIG. 1), the user 401 can determine whether there is a signal being received indicative of a leak, e.g., in the 40K Hertz range. In addition, the user 401 can also wear the listening device 308 (FIG. 3), and determine, based upon what he hears, whether there is a notable signal in the vicinity. If the user 401 is unsure about the nature of the sound that he hears, the user 401 can select to hear, e.g., a sample air leak from the sound byte data 222 (FIG. 3) and audibly compare what he is hearing with the sounds stored in memory 302.

Figure 5:
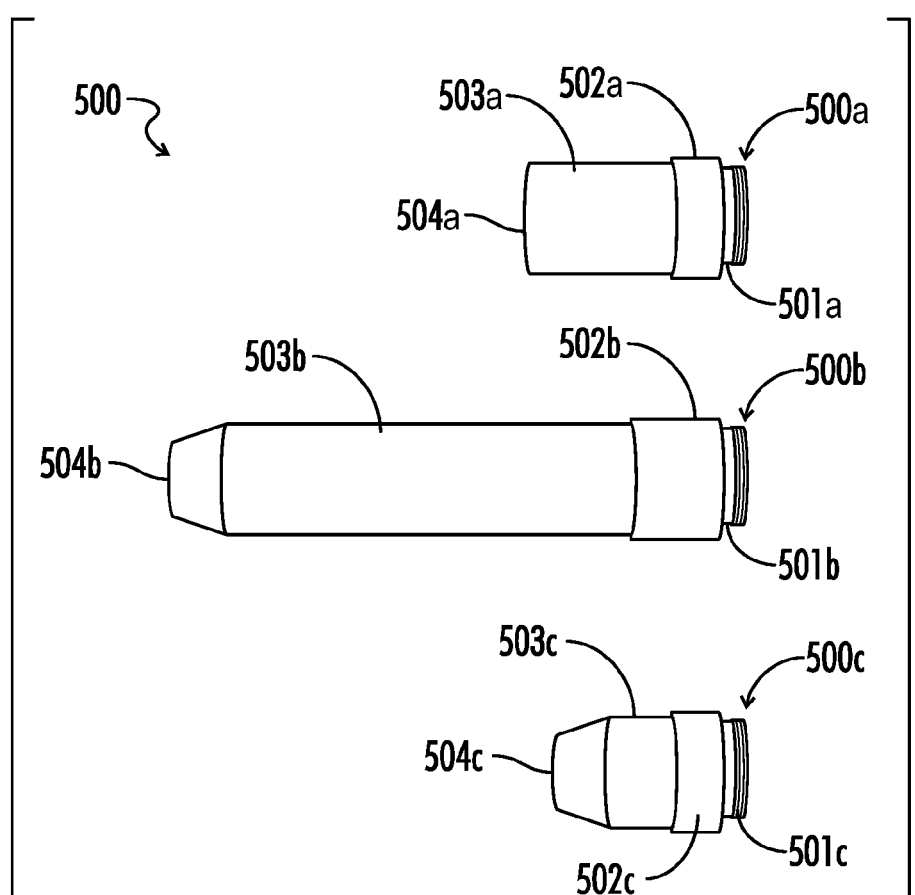
FIG. 5 depicts three exemplary embodiments of receiver heads for the handheld ultrasound detection apparatus, such as is depicted in FIG. 1.

FIG. 5 depicts three exemplary embodiments 500*a*, 500*b*, and 500*c* of receiver heads that can be connected to the threaded cylindrical structure 201 (FIG. 2). The receiver heads 500*a*, 500*b*, and 500*c* connect to the threaded cylindrical structure 201 (FIG. 1) on the apparatus 100 (FIG. 1) and facilitate reception of ultrasound signals (not shown). In this regard, the receiver heads 500*a*, 500*b*, and 500*c* extends the "reach" of the apparatus 100. Each receiver head 500*a*, 500*b*, and 500*c* is hollow having an open at their ends, i.e., at the distal end of the receiver heads 500*a*, 500*b*, and 500*c*.

The receiver head 500*a* comprises a threaded end 501*a*, a gripper portion 502*a*, a shaft 503*a*, and a receiving end 504*a*. In this embodiment, the threaded end 501*a* comprises a male thread that mates with the female threaded cylindrical structure 201 (FIG. 1). The gripper portion 502*a* comprises a raised generally rough surface that is easily grippable by the user's fingers to install and remove the receiver head 500*a* from the apparatus 100.

The shaft 503*a* is a generally cylindrical extender with a hollow, generally cylindrical bore and is integrally formed with the threaded end 501*a*, the gripper portion 502*a*, and the receiving end 504*a*. In one embodiment, the shaft 503*a* is one and one-half (1½) inches long with a hollow bore. In other embodiments, other dimensions can be used. The shaft 503*a* may be fabricated from stainless steel or other rigid materials. In one embodiment the shaft 503*a* is fabricated from a non-conductive material such as Delrin so as to avoid arcing when testing for corona discharge of electrical circuits or in electrical panels.

In another embodiment, the shaft 503*a* and/or the receiving end 504*a* is fabricated from a magnetic material. A magnetic receiving end 504*a* may be desirable when testing certain components, such as bearings, because the end 504*a* is attracted to and may temporarily affix to the jacket of the bearing. While the end 504*a* is temporarily affixed to the component under test, the sound quality may be greater and the incidence of undesirable sounds being received may be decreased.

The receiving end 504*a* is open-ended for pointing at and receiving ultrasonic signals. The receiving end 504*a* is a generally straight cylindrical end. As discussed below with respect to the receiving end 504*b*, other embodiments have tapered ends.

The receiver head 500*b* comprises a shaft 503*b* that is longer than the shaft 503*a* of the receiver head 500*a*. A longer shaft may be desirable, for example, when testing for leaks among a plurality of pipes in a small area. In this regard, the elongated shaft 503*b* may fit in amongst multiple pipes to test around joints and seals. In one embodiment, the shaft 503*b* is five inches in length, though other lengths could be used.

The receiver head 500*b* further comprises a tapered receiving end 504*b*. The tapering of the receiving end 504*b* serves the purpose of narrowing the end to enable it to squeeze into tighter spaces. The tapering further serves to funnel the ultrasonic signals into the receiver 200 and also reflects undesirable signals away from the receiver head 500*b*.

The receiver head 500c also comprises a tapered receiving end 504c. The receiving end 504c is integrally formed with the elongated shaft 503c and a gripper portion 502c.

Each of the receiver heads 500a, 500b, and 500c essentially extend the reach of the receiver 200 contained handheld ultrasound detection apparatus 100. In this regard, the receiver heads 500a, 500b, and 500c are such that input is more focused in the direction at which the receiving end is pointed. Thus, the ultrasound energy received by the receiver 200 has a more pronounced effect because the ultrasound energy is directed at the receiver 200 by the receiver heads 500a, 500b, and 500c.

Figure 6:
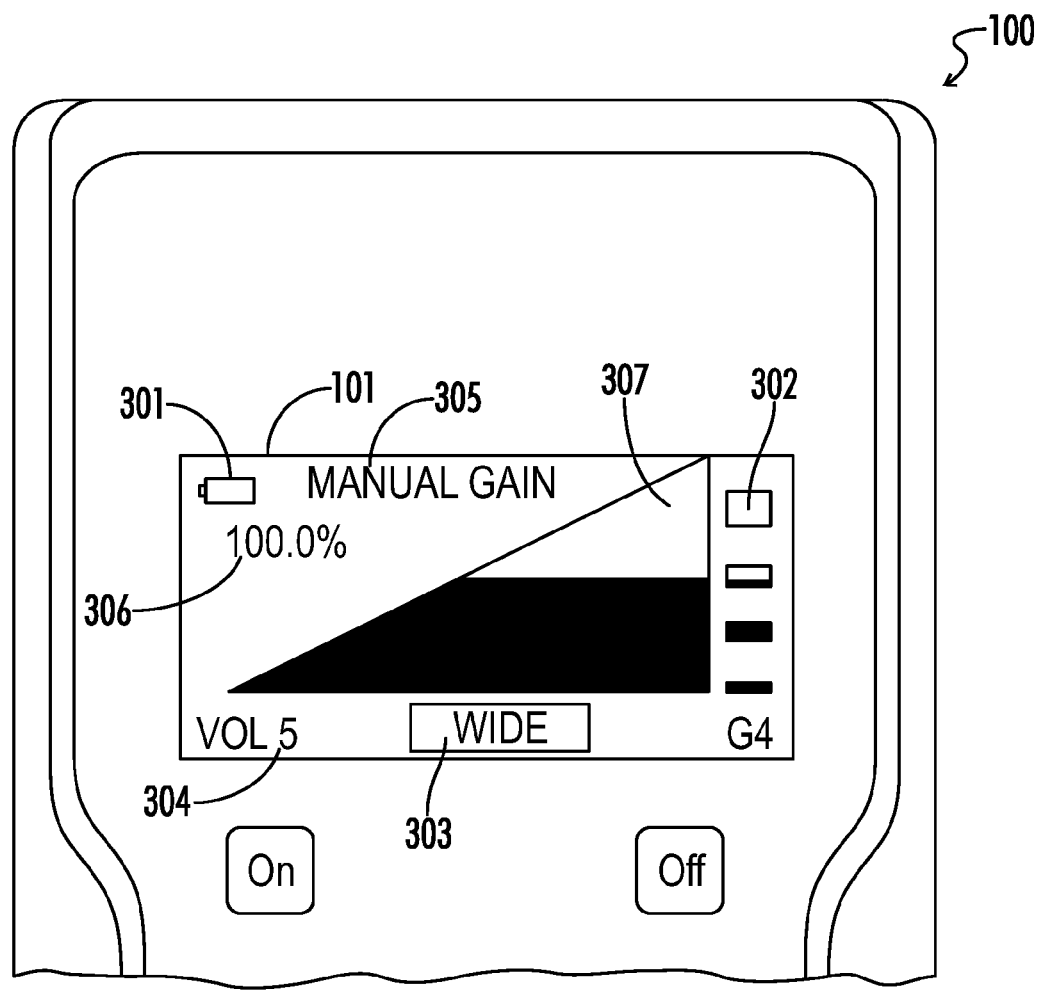
FIG. 6 depicts an exemplary display device of the apparatus depicted in FIG. 1.

FIG. 6 depicts an exemplary display device 101 according to an embodiment of the apparatus 100. The display device 101 comprises a battery level indicator 301 which displays graphically the general amount of battery power remaining. Display device 101 further comprises a volume indicator 304 which displays the current volume setting of the apparatus 100. A mode indicator 303 displays whether the apparatus 100 is in Wide or Narrow mode. Signal intensity bars 302 and a signal intensity window 307 display graphically the intensity level of a signal received.

The display device 101 further comprises a saturation level indicator 306 that indicates the saturation level of the electronics. The display device 101 further comprises a mode indicator 305 that indicates that the apparatus 100 is in "Manual Gain" mode.

Figure 7:
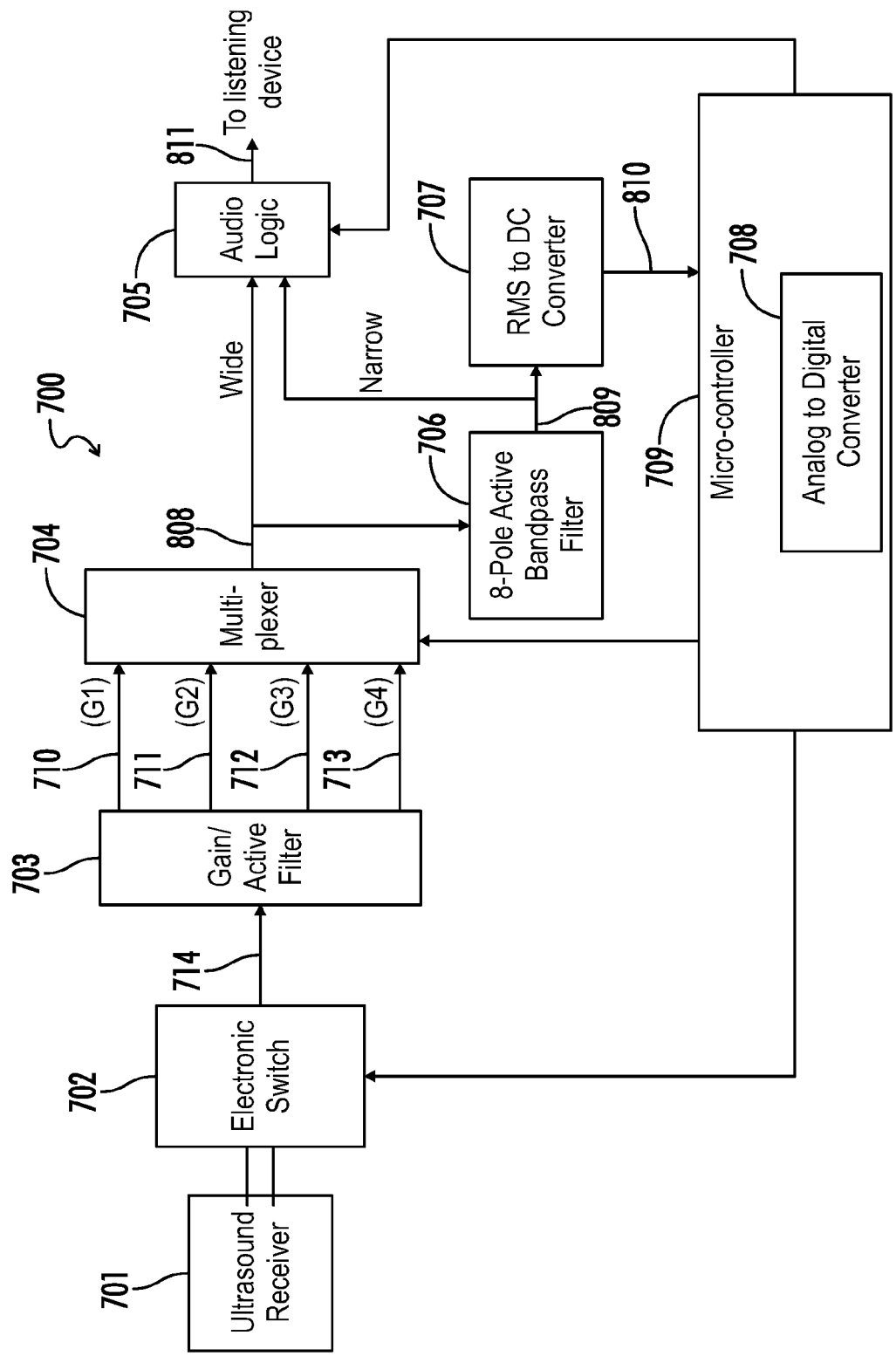
FIG. 7 is a block diagram depicting exemplary circuitry of the ultrasound detection apparatus such as depicted in FIG. 1.

FIG. 7 depicts an exemplary circuit 700 in accordance with an embodiment of the leak detection apparatus of FIG. 1. The circuit comprises an ultrasound receiver such as for example a transducer 701, an electronic switch 702, and a gain/active filter 703. In addition, the circuit comprises a multiplexer 704, an 8-pole active band pass filter 706, a root mean square (RMS) to digital converter 707, and an analog to digital converter 708. The circuit 701 is further controlled by a micro-controller 709.

The transducer 701 detects sound present in the area of the transducer 701, i.e., the transducer 701 listens for sound. When the leak detection apparatus 100 is initially powered on, the circuit 700 enters calibration mode. In calibration mode, the transducer 701 is disconnected from the circuit 700. In this regard, when the circuit 700 is powered on, the micro-controller 709 transmits a signal to the electronic switch 702, and the electronic switch 702 disconnects the transducer 701 from the circuit 700.

During calibration, the micro-controller 709 grounds the electronic components within the gain/active filter 703. The micro-controller 709 then measures a plurality of direct current (DC) offset values and an inherent noise floor value for the circuit 700. The offset values and the noise floor values are eventually subtracted out of any signal received through the transducer 701.

Figure 8:
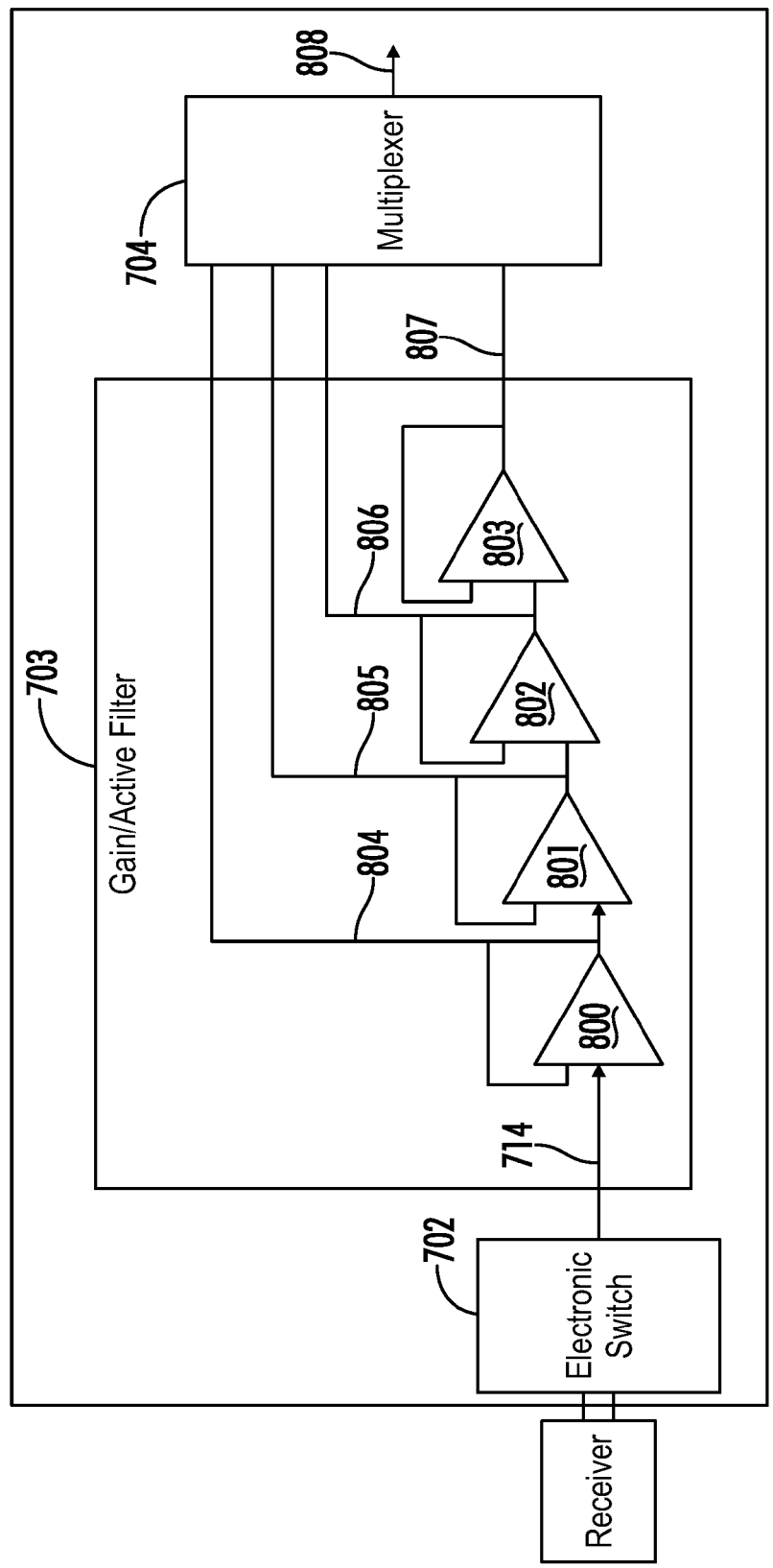
FIG. 8 is a block diagram depicting exemplary gain/active filter circuitry of the exemplary circuitry of FIG. 7.

In one embodiment, the gain/active filter 703 is configured and constructed as shown in FIG. 8. In such an embodiment, the gain/active filter 703 comprises a plurality of amplifiers 800-803 arranged in a cascading fashion. Notably, each amplifier 800-803 exhibits a particular gain and each amplifier 800-803 corresponds to a differing gain range to be applied to a signal 714 (FIG. 8), which is described further herein. Further note that the range of the signals that the gain/active filter 703 can manipulate is in the 130 decibel (dB) range, which translates into the ability of the gain/active filter 703 handling signals in the 0.1 micro Volts ($\mu$V) to 0.5 Volts (V) range.

During calibration mode, the micro-controller 709 (FIG. 7) samples the outputs of each of the amplifiers 800-801 to determine an offset value for each amplifier. Each amplifier 800-801 comprises a power supply (not shown), and while during calibration mode the amplifiers 800-803 are grounded, there still exists some voltage offset value, e.g., 3 millivolts (mV), at the outputs of the amplifiers 800-803. Such offset value is stored by the micro-controller 709 and eventually subtracted from any signal received through the transducer 701, during operation. In addition, each of the amplifiers 800-803 generates internal noise, and the micro-controller 709 measures the noise generated by each of the amplifiers 800-803, and also subtracts a noise floor value based upon the internal noise from the signal 714 received through the transducer 701 (FIG. 7), during operation.

Referring to FIG. 7, after calibration the microcontroller 709 transmits a signal to the electronic switch 702 and the electronic switch 702 then allows signals from the transducer 701 to be transmitted to the gain/active filter 703. The gain/active filter 703 is configured and constructed to filter frequency components in the analog signal 714 at or around 38.4 kilo Hertz (kHz).

During operation, the transducer 701 detects sound and outputs the analog signal 714 indicative of the sound received to the gain/active filter 703. Based upon the analog signal 714 received, the gain/active filter 703 generates four signals 710-713 filtered at or around 38.4 kHz, each signal exhibiting a differing gain. With reference to FIG. 8, in one embodiment, the gain/active filter 703 is constructed and configured with the four amplifiers 800-803, as described hereinabove.

The analog signal 714 (FIG. 8) is input into amplifier 800, and the amplifier 800 applies a particular gain to the analog signal 714. An output analog signal 804 of the amplifier 800 exhibiting the applied gain is transmitted to the multiplexer 704 and serves as input to the next amplifier 801 in the cascade of amplifiers 800-803. The amplifier 801 applies a particular gain to the analog signal 804. An output analog signal 805 of the amplifier 801 exhibiting the applied gain is transmitted to the multiplexer 704 and serves as input to the next amplifier 802 in the cascade of amplifiers 800-803. The amplifier 802 applies a particular gain to the analog signal 805. An output analog signal 806 of the amplifier 802 exhibiting the applied gain is transmitted to the multiplexer 704 and serves as input to the next amplifier 803. The amplifier 803 applies a particular gain to the analog signal 806, and the analog signal 806 is output to the multiplexer 704.

Referring to FIG. 8, the multiplexer 704 receives the four analog signals 804-807 from the gain/active filter 703. Additionally, each analog signal 804-807 is indicative of the analog signal 714 exhibiting a particular gain. In one embodiment, each gain exhibited by each signal 804-807 is different. Furthermore, signal 807 exhibits the greatest amount of gain, signal 806 exhibits a gain less than signal 807, but greater than signal 805, and signal 805 exhibits a gain less than signal 806, but greater than signal 804. Therefore, the gain/active filter 703 generates signals 804-807 of varying gain ranges based upon the original analog signal 714, which are input to the multiplexer 704.

The micro-controller 709 selects which analog signal 804-807 is output as the multiplexer's output 808. Such output may be referred to as the "Wide" range output signal. When the circuit 700 is powered up and calibration is complete, the analog signal 808 output from the multiplexer 704 is the analog signal 807, which is the signal exhibiting the largest amount of applied gain through the amplifiers 800-803.

The output signal 808 is transmitted to audio logic 705, which is described further herein, and the output analog signal 808 is also passed through an 8-pole active filter 706 to further eliminate extraneous noise components that may be in the signal 808. The 8-pole active filter 706 filters the signal 808 at or around 38.4 kHz and outputs another analog signal 809, which may be referred to as the "Narrow" range output analog signal.

The Narrow range output analog signal 809 is transmitted to the audio logic 705, which is described further herein, and the Narrow range output analog signal 809 is also transmitted to the root mean square (RMS) to DC converter 707. The RMS to DC converter 707 rectifies the analog signal 809, so there are no longer negative components in the signal 809. The RMS to DC converter 707 further smoothes the signal 809 to an approximate steady constant signal.

The rectified smoothed signal is output 810 that is then sampled by the A/D converter 708. Such sampling indicates the maximum voltage amplitude of the output signal 810. If the signal 810 reaches a threshold value, which is described further herein, then the micro-controller 709 transmits a signal to the multiplexer 704 to select one of the other signals 710-712 as the output 808 of the multiplexer 704. Thus, the micro-controller 709 compares the digital values obtained from the A/D converter 708 to a threshold value to determine whether the signal 808 output from the multiplexer should be switched to one of the other signals 710-712. Notably, as indicated hereinabove, initially signal 714 is output as signal 808.

In one embodiment, the threshold value is 3 Volts. Thus, if the digital value indicative of the signal 810 is substantially close to 3 Volts, e.g., if the signal is at 99% or 2.97 Volts, then the micro-controller 709 transmits a signal to the multiplexer 704, and the multiplexer 704 transmits as its output the next analog signal 712 having a smaller gain than the signal 713. This process continues throughout operation.

Note that the Wide range output signal 808 is output from the multiplexer 704, and the Wide range output signal 808 exhibits a particular gain applied by the gain/active filter 703. The output signal 808 is indicative of the input signal 714 having some noise components removed. Further note that the Narrow range output signal 809 is also indicative of the input signal 714; however, additional noise components are removed by the 80 pole active band pass filter 706 above that which was removed by the gain/active filter 703.

During operation, a user (not shown) can select the "Wide" button 107 (FIG. 1) or the "Narrow" button 108 (FIG. 1). When the "Wide" button 107 is selected, the micro-controller 709 transmits a signal to the audio logic 705 indicating that the Wide range output signal 808 is to be transmitted to any connected listening device 120, 121 (FIG. 1B), and the audio logic 705 transits as a signal 811 the Wide range analog signal 808. Furthermore, when the "Narrow" button 108 is selected, the micro-controller transmits a signal to the audio logic 705 indicating that the Narrow range output signal 809 is to be transmitted to any connected listening device 120, 121, and the audio logic 705 transmits as the signal 811 the Narrow range analog signal 809. This allows the user to listen to the signal 714 being detected in two differing modes with some noise removed and with additional noise removed.

Note that the output signals 710-713 may be represented by G1, G2, G3, and G4, respectively. Thus, with reference to FIG. 6, during operation the micro-controller 709 can display an indicator 624 and a symbol 620-623 indicating which gain range the circuit 700 is operating in. In addition, the display 101 may comprise an indicator 606, which indicates at what percentage of the gain range the circuit 700 is operating, which may also be indicated by the graphical component 607. In the exemplary display 101, the circuit 700 is operating in G4 at 50%, as indicated by indicator 624 and 606, respectively.

Figure 9:
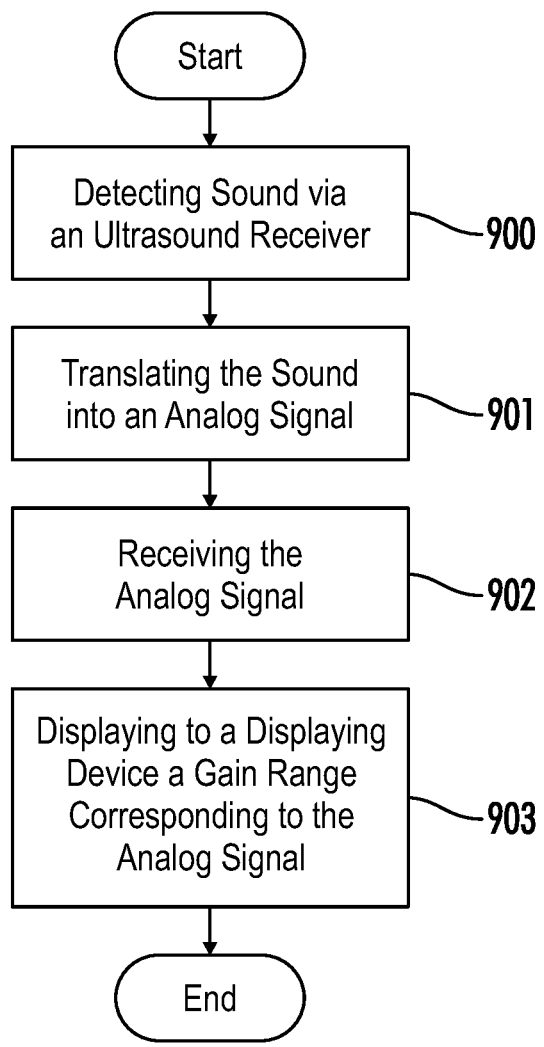
FIG. 9 is a flowchart illustrating an exemplary method in accordance with an embodiment of the present disclosure.

FIG. 9 depicts a flowchart of an exemplary method in accordance with an embodiment of the present disclosure. The first step 900 in the method is detecting sound via a transducer 701 (FIG. 8). The next step 901 is translating the sound into an analog signal 714 (FIG. 8).

Step 902 is detecting the analog signal indicative of the sound detected by the transducer 701. Step 903 is displaying to the display device 101 (FIG. 1) a gain range corresponding to the analog signal.

Figure 10:
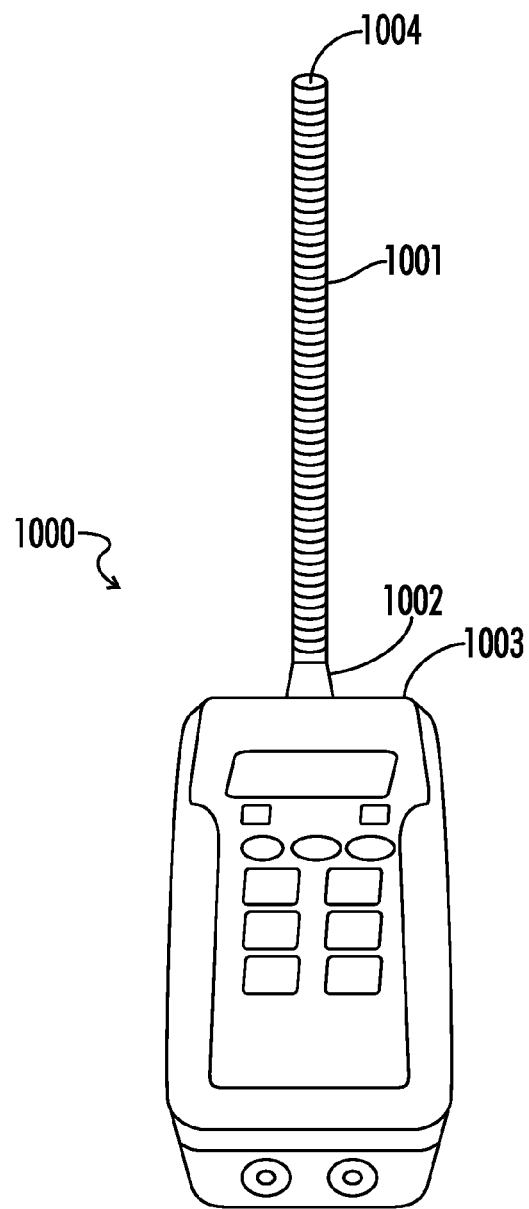
FIG. 10 depicts a front bottom perspective view of a handheld ultrasound detection apparatus having a flexible tube in accordance with an embodiment of the present disclosure.

FIG. 10 depicts a back end perspective view of a handheld ultrasound detection apparatus 1000 in accordance with another embodiment of the present disclosure. In such an embodiment, the handheld ultrasound detection apparatus 1000 comprises a housing 1003. The handheld ultrasound detection apparatus 1000 further comprises a flexible tube 1001 connected at its proximal end to the housing 1003.

Notably, the handheld ultrasound detection apparatus 1000 is substantially similar to the device 100 depicted in FIG. 2. In this regard, the flexible tube 1001 comprises a base 1002, and there is a receiver (not shown), similar to the receiver 200 (FIG. 1) within the base 1002.

In one embodiment, the base 1002 may comprise threading. In such an embodiment, the flexible tube 1001 may also comprise threading (not shown), and the flexible tube 1001 is threadedly coupled to the base 1002. In other embodiments, the flexible tube 1001 may be attached to the housing 1003 in other ways, for example, the flexible tube 1001 may be permanently mounted to the base 1002 via a weld.

During use, the receiver (not shown) receives sound waves that travel through the flexible tube 1001. Notably, when an opening 1004 of the flexible tube 1001 is pointed in a direction of a sound, the sound waves (not shown) enter the flexible tube 1001 through the opening 1004 and travel through the tube to the receiver. Provision of the flexible tube 1001 tends to decrease the effect of ambient noise when a user (not shown) is attempting to locate a source (not shown) of a particular sound.

Figure 11:
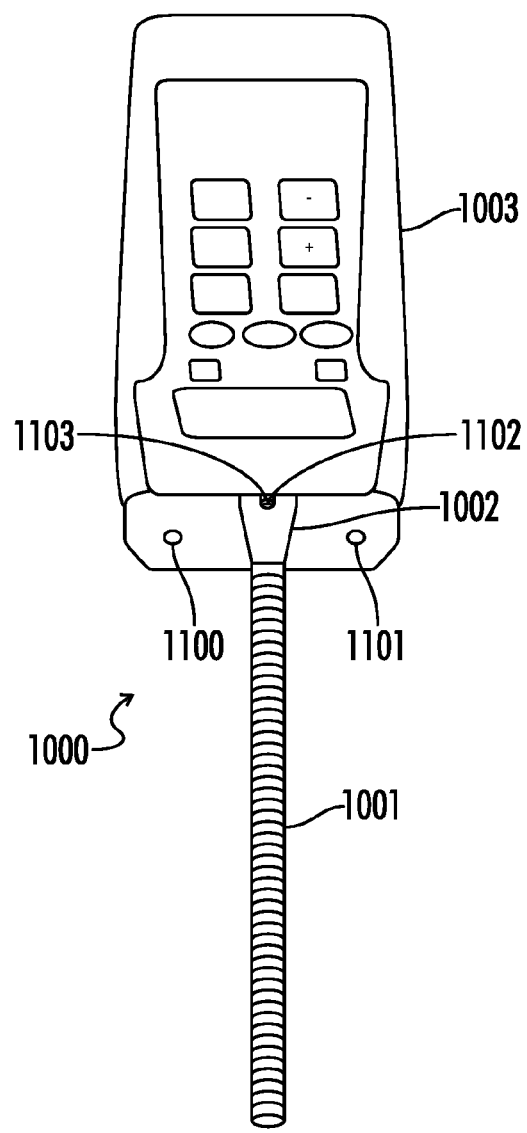
FIG. 11 depicts a front top perspective view of the handheld ultrasound detection apparatus of FIG. 1.

FIG. 11 depicts a front top perspective view of the handheld ultrasound detection apparatus 1000. In this regard, the flexible tube 1001 comprises the base 1002, and the base 1002 is mounted to the housing 1003. The apparatus 700 further comprises a laser 1103 and a detector 1102, which behave similar to the laser 202 (FIG. 2) and detector 205 (FIG. 2), described hereinabove. Such laser 1103 and detector 1102 are mounted to the housing 1003.

In addition, the apparatus 1000 further comprises lighting devices 1100 and 1101, which emit visible light, similar to the lighting devices 203 (FIG. 2) and 204 (FIG. 2) described hereinabove. Such lighting devices 1100 and 1101 are mounted to the housing 1003.

Notably, the flexible tube 1001 and the base 1002 are mounted below the laser 1103/detector 1102 combination. In addition, the flexible tube 1001 and the base 1002 are mounted between the visible lighting devices 1100 and 1101.

Figure 12:
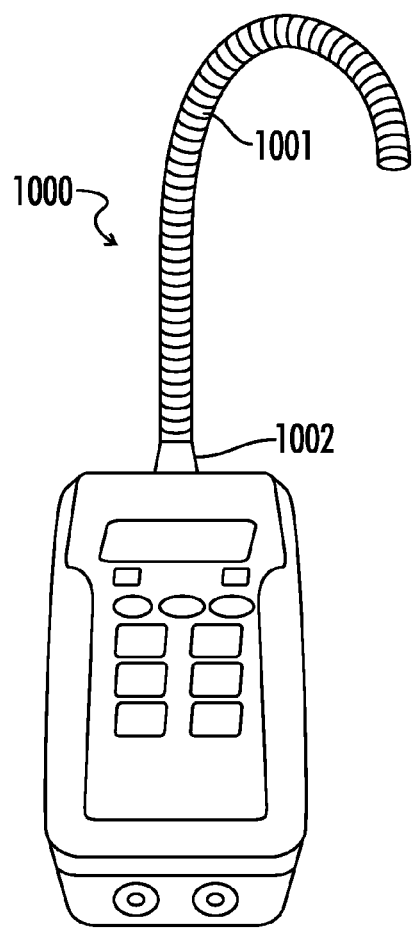
FIG. 12 depicts the handheld ultrasound detection apparatus of FIG. 1 showing a one-way deformation of the flexible tube.

FIG. 12 depicts the apparatus 1000 showing the flexible tube 1001 in an arc-shape. Such a bend would enable the user (not shown) of the apparatus 1000 to detect sound around a corner (not shown), that may otherwise be undetectable. In this regard, such bend in the flexible tube 1001 facilitates positioning of the flexible tube 1001 around obstacles so that it is better exposed to ultrasound waves.

Figure 13:
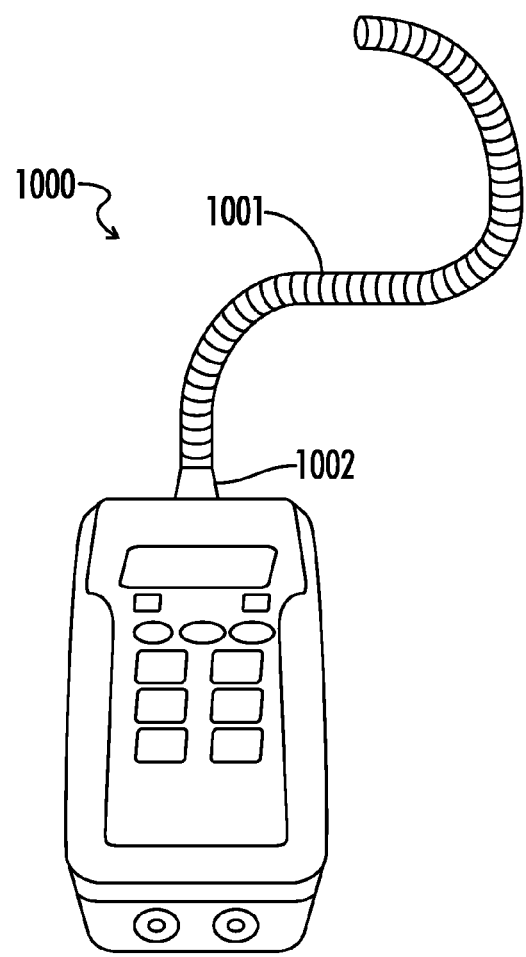
FIG. 13 depicts the handheld ultrasound detection apparatus of FIG. 1 showing a two-way deformation of the flexible tube.

FIG. 13 depicts the apparatus 1000 showing the flexible tube 1001 further bent in such way as to have to arc-shaped bends. Such bends, again, would enable the user of the apparatus 1000 to detect sound in areas that may otherwise be concealed with obstacles. In this regard, such bend in the flexible tube 1001 facilitates positioning of the flexible tube 1001 around obstacles so that it is better exposed to ultrasound waves.

Figure 14:
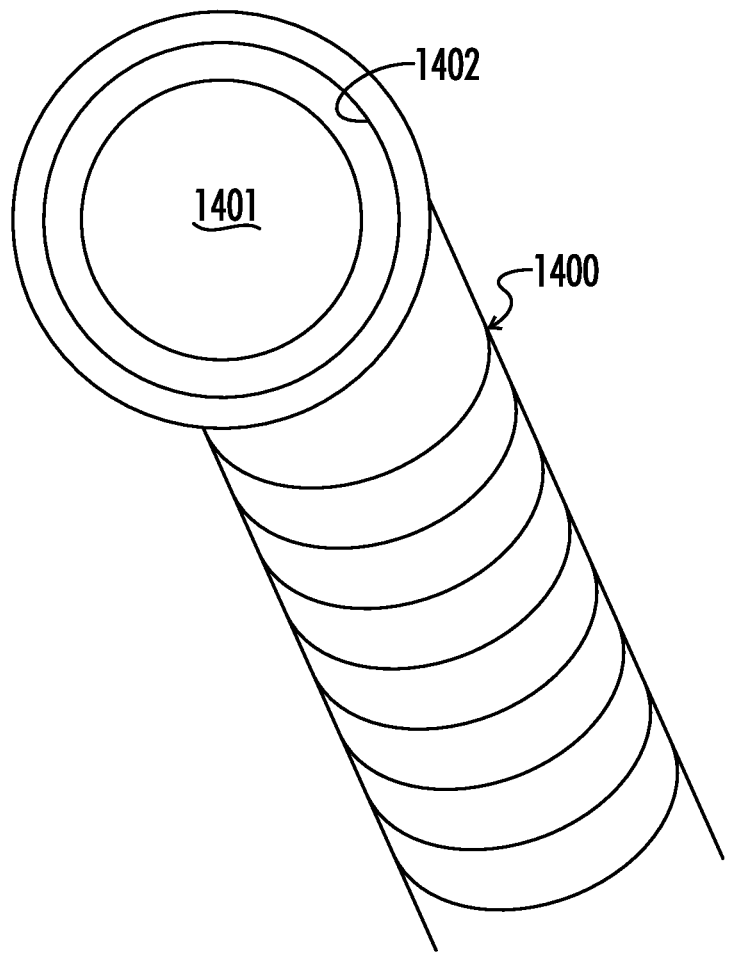
FIG. 14 depicts an exemplary end of a flexible tube having a receiver therein in accordance with another embodiment of the present disclosure.

FIG. 14 depicts a distal end of a flexible tube 1400 in accordance with another embodiment of the present disclosure. In such an embodiment, a receiver 1401 is mounted in an opening 1402 in the distal end of the flexible tube 1400. The mounting of the receiver 1401 in the opening 1402 of the flexible tube 1400 is in contrast to the embodiment described hereinabove wherein the receiver 200 (FIG. 2) is mounted in the base 1002 (FIG. 7) that is coupled to the housing 1003 (FIG. 7).

In the embodiment described with reference to FIG. 13, wires (not shown) travel through the flexible tube 1400. The wires are then attached to a printed circuit board (not shown) within the handheld ultrasound detection apparatus 1000.

Figure 15:
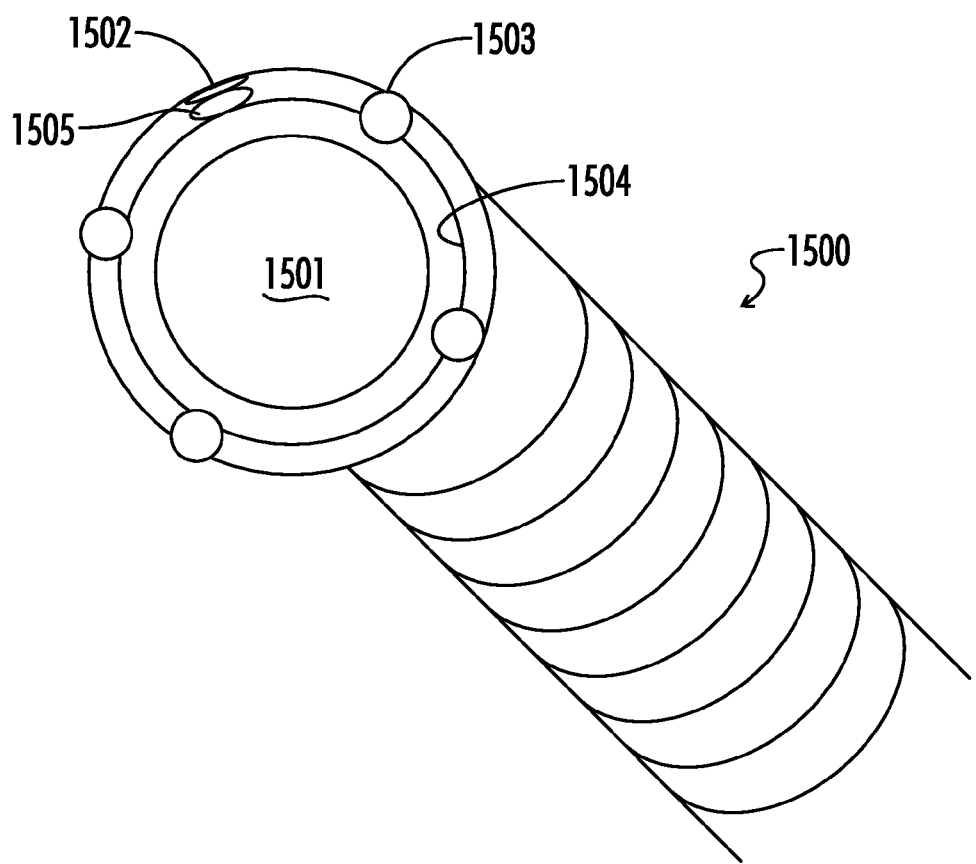
FIG. 15 depicts another exemplary end of a flexible tube having a receiver, a laser light, and a plurality of visible lights in accordance with another embodiment of the present disclosure.

FIG. 15 depicts a flexible tube 1500 in accordance with another embodiment of the present disclosure. In such an embodiment, a receiver 1501 is mounted in an opening 1504 in the flexible tube 1500 similar to the flexible tube 1400 (FIG. 14). In addition, however, the flexible tube 1500 further comprises a laser 1502 and a detector 1505, which operate similar to the laser 202 (FIG. 2) and the detector 205 (FIG. 2) described hereinabove. Also, the flexible tube 1500 comprises a plurality of visible lighting devices 1503.

Figure 16:
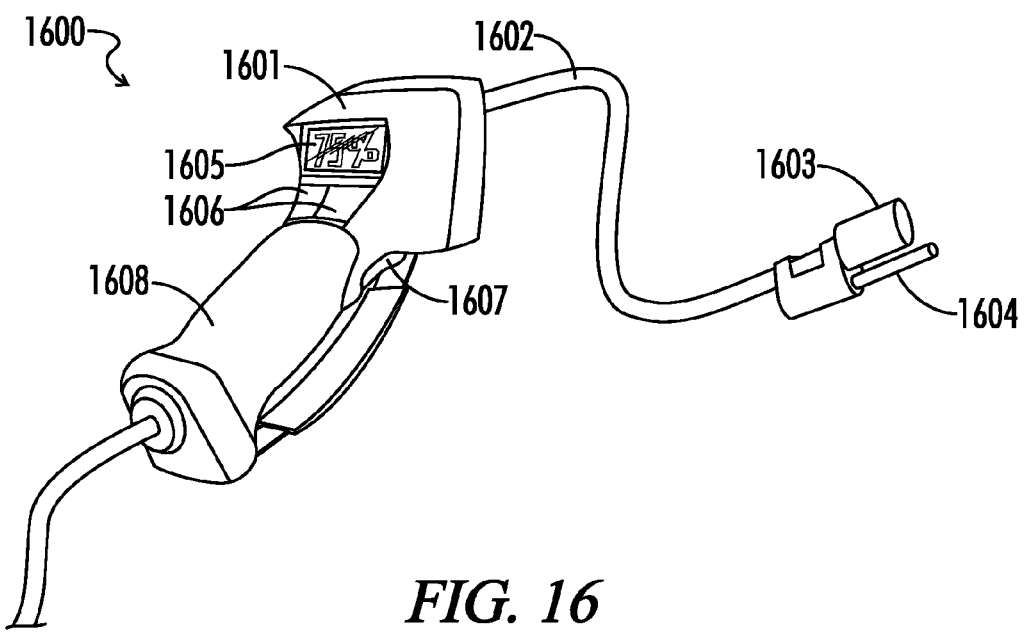
FIG. 16 is an isometric view of another embodiment of a handheld ultrasound detection apparatus in accordance with the present invention.
Figure 17:
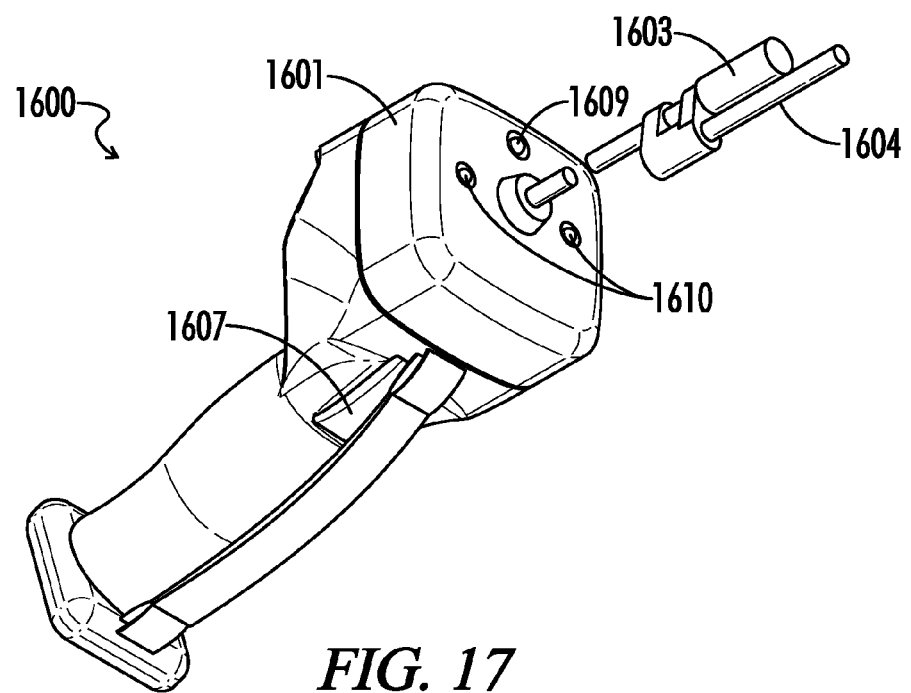
FIG. 17 is an isometric view another embodiment of a handheld ultrasound detection apparatus in accordance with the present invention.

Referring now to FIGS. 16 and 17, additional embodiments of an apparatus within the scope of the present disclosure may include an ultrasound measurement unit 1600 with a portable housing 1601 about or within which is disposed a flexible tube 1602, a sound cup 1603 on a distal end of the flexible tube relative to the housing, a distance member 1604, a display portion 1605, user interface components such as buttons, dials, etc. 1606, actuators such as for example a trigger-style button 1607, a user grip portion 1608, a position indicator such as for example a laser pointer 1609, and one or more status indicators such as for example LED lights 1610.

The measurement unit 1600 as represented in FIGS. 16 and 17 may further include control circuitry and program logic (not shown) so as to perform digital filtering, measurement, and output steps as further described herein. Alternatively, a distributed processing apparatus may supplement the unit 1400 with a separate housing (not shown) that is communicatively and functionally linked to the unit 1600 and includes appropriate control circuitry and program logic disposed therein.

The apparatus may further include another unit (not shown) with a portable housing and an optical scanner or the equivalent as is known in the art along with appropriate software, firmware, logic, etc., for reading barcode labels, QR codes, etc. Alternatively, equivalent functionality may be made available by appropriate configuration of the first unit 1600, or the apparatus itself may function in association with a mobile computing device such as for example a smart phone having optical barcode scanning capability as is further known in the art. The apparatus may in this fashion obtain or otherwise receive information at the time of sound data collection with respect to the particular piece of equipment of point of inspection, if such information is made available in the form of a predefined barcode label, QR code or the like.

Various methods of ultrasound detection as performed by the measurement unit 1600 may be substantially identical to those previously described above. Additional steps and features as may be made available or otherwise performed by a unit 1600 within the scope of the present invention may be further described herein.

Generally stated, an apparatus according to the present disclosure may measure air pressure created from the intensity of the work at the source, rather than mere sound measurement. Sound is but a medium by which we can measure that work in a non-contact manner. One or more piezoelectric transducers disposed within the flexible tube 1602 are effective to receive analog ultrasound signals and convert the signals to electrical (digital) impulses that are then filtered and amplified by appropriate circuitry and digital logic components.

The device may generate sound data files based on the filtered and amplified digital impulse signals for internal measurement, conversion and display, and further for external transmission to a remote server or other device for storage and analysis as further described below.

As disclosed above, various embodiments of the device may further or alternatively convert the filtered and amplified digital impulses back to analog signals for user examination of the represented sound data via for example earphones.

Given the potential importance of very small changes in the work at the source, measurement methods may be provided to effectively communicate those changes to users (e.g., customers, technicians, administrators). In a particular embodiment, a measurement method may be provided to clearly reflect a 10% change in the amount of work in a source as close to 10% as possible, a 20% change in work as close to 20% as possible, and so on. Presenting this in decibels requires the user to do an unnecessary calculation to convert the logarithmic scale to the required linear scale. As a user may typically not be conversant with decibels or have easy access to a conversion tool, presenting the intensity of the work in a percentage format is found to be a much more effective form of communication. Percentage measurements also support simple charting, statistical analytics, and comparisons.

In presenting simple to understand changes in the amount of work at a source, it is beneficial to eliminate points of confusion or error in understanding the percentage value. Due to the mechanics of the source of the sound, different sources of work produce intensity that varies depending on the frequency by which it is measured. In embodiments of the present invention wherein a device is optimized to measure sounds created by mechanical friction, a frequency band may be defined to allow for adequate transmission of sounds from that particular type of source.

Further, wherein various embodiments of a device within the scope of the present invention can distinguish sound from mechanical friction, the impacts of sound from air movement and electricity are also considered in the defined frequency range. The device is tuned to a frequency where sounds from all three sources are prominent but not optimal individually. This allows for measurement and differentiation of sound from each of these sources. As the intensity of measurement with a device changes based on the frequency, the device may prevent (or otherwise not enable) a user from changing the frequency and may also automatically calibrate and tune the device to prevent errors.

In various embodiments, a plurality of devices may be programmed with common calibration/tuning factors to harmonize output from the various devices, and otherwise prevent or at least substantially minimize the effects of user error where for example a centralized server system is implemented to receive and analyze the sound signatures generated from the devices. By disabling user selection features, an ultrasound measurement system according to the present disclosure may thereby minimize variance in measurement across a spectrum of devices, with respect to analogous applications and their associated frequency-magnitude curves (see, e.g., FIGS. 19-22).

To measure small changes in intensity, the resolution of a device may be set to a narrow range of sound intensity that is measured. At the lower or quietest side of the measurement range, the device may measure sound intensity significantly below the amount normally considered as the threshold of hearing, or close to the absence of sound in our frequency range. However, this also may cause a restriction on the maximum amount of sound intensity that can be reflected on the percentage scale. To address this, program logic and filtering may be provided to allow expansion of the measurement range to 400% of the normal maximum scale. As the measurement increases from zero to 400%, the device maintains the linearity of the scale so as to ensure the easy-to-understand representation to the user as to the amount of energy being generated at the source.

For the purpose of ensuring accurate understanding of the zero to 400% scale, the device may be placed in an 'auto' mode that uses analytics to manage the transition between what is normally referred to as gain fields. In some embodiments of a device according to the present invention, a user may also be enabled to selectively freeze the device into a single gain field thus restricting the device to a single zero to 100% range.

Since intensity is greatly affected by changes in angle and distance, another aspect of embodiments of the present invention is to provide a non-contact transducer as close to the source of the sound as possible. A sound cup 1603 is coupled to the device 1600 that creates a 1" standard measurement point from the source with as close to a zero degree angle as possible. This facilitates consistency of measurement from one source to another and 'pre-defines' the impacts of the loss of intensity due to distance. Additionally, the sound cup 1603 may be made from materials that 'block' sound from sources other than the intended source of the sound, thus significantly improving the measurement of the intended source.

Figure 18:
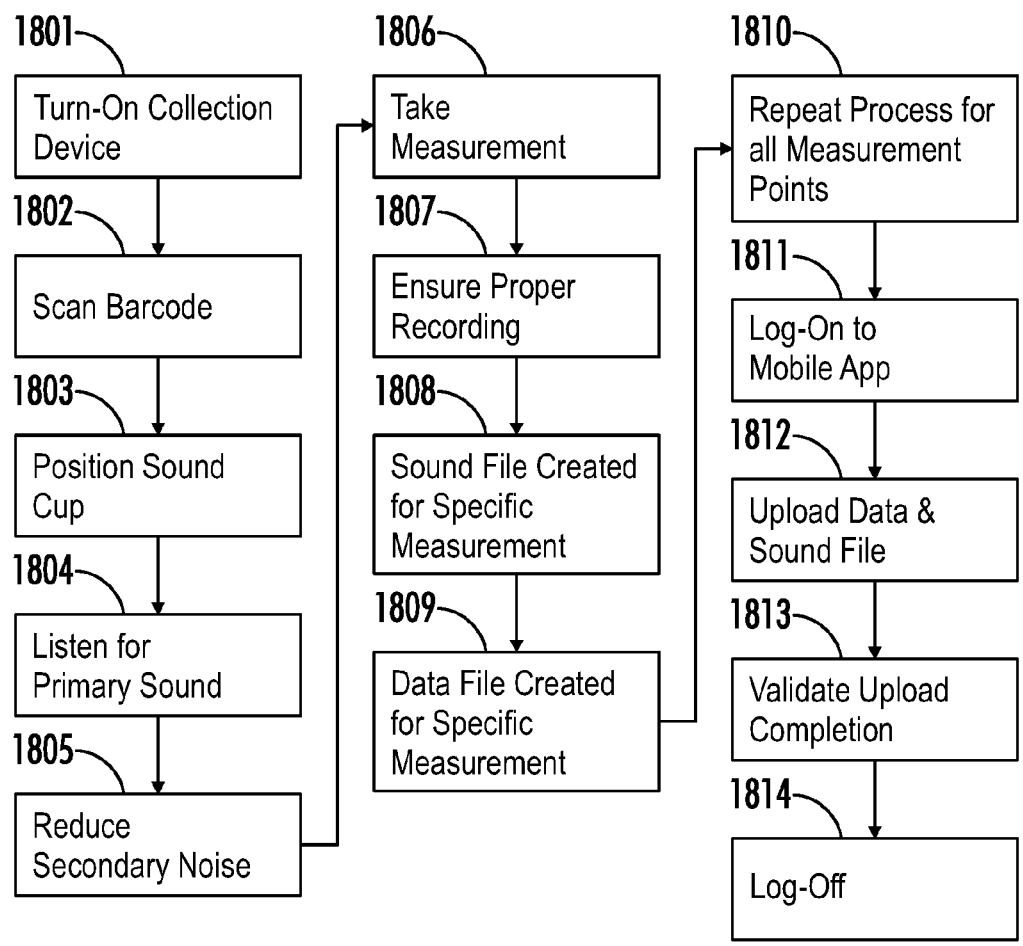
FIG. 18 is a flowchart representing an exemplary data collection process in accordance with embodiments of the present invention.
Figure 19:
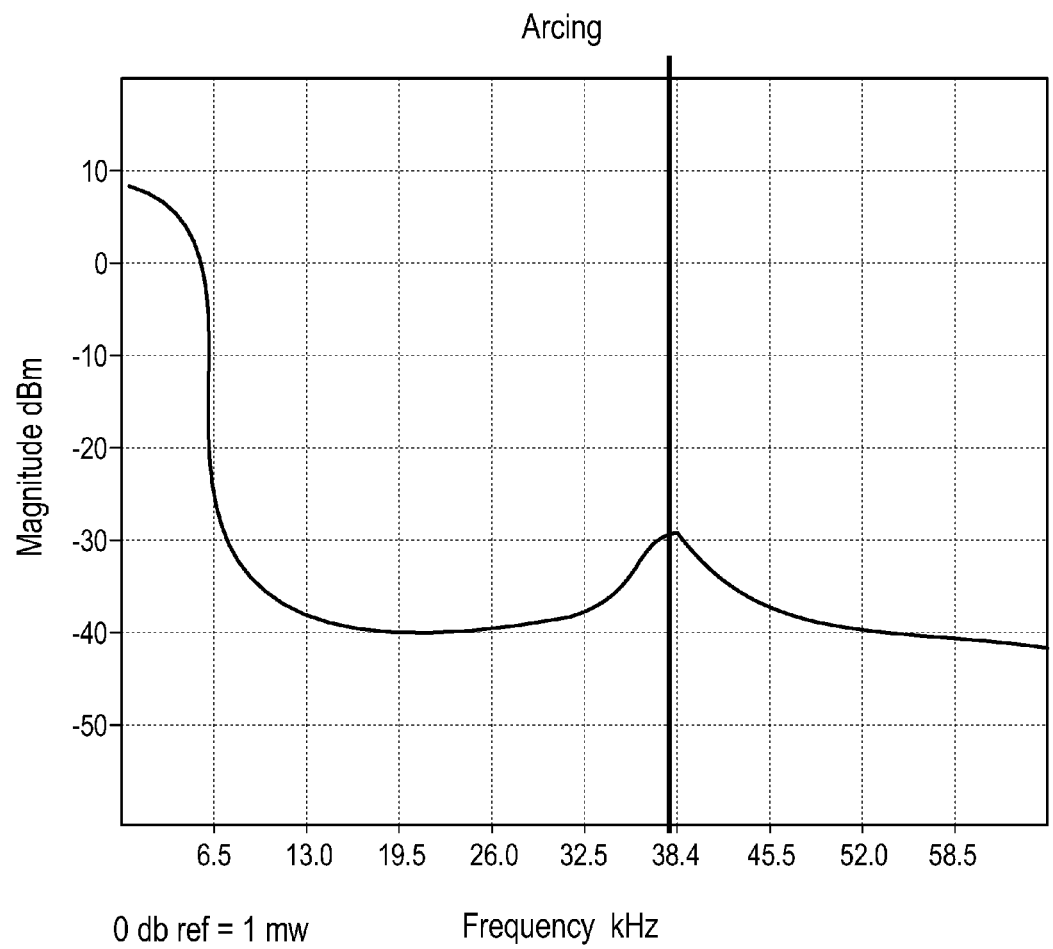
FIGS. 19-22 are graphical diagrams representing frequency versus magnitude for various practical applications of the present invention.
Figure 20:
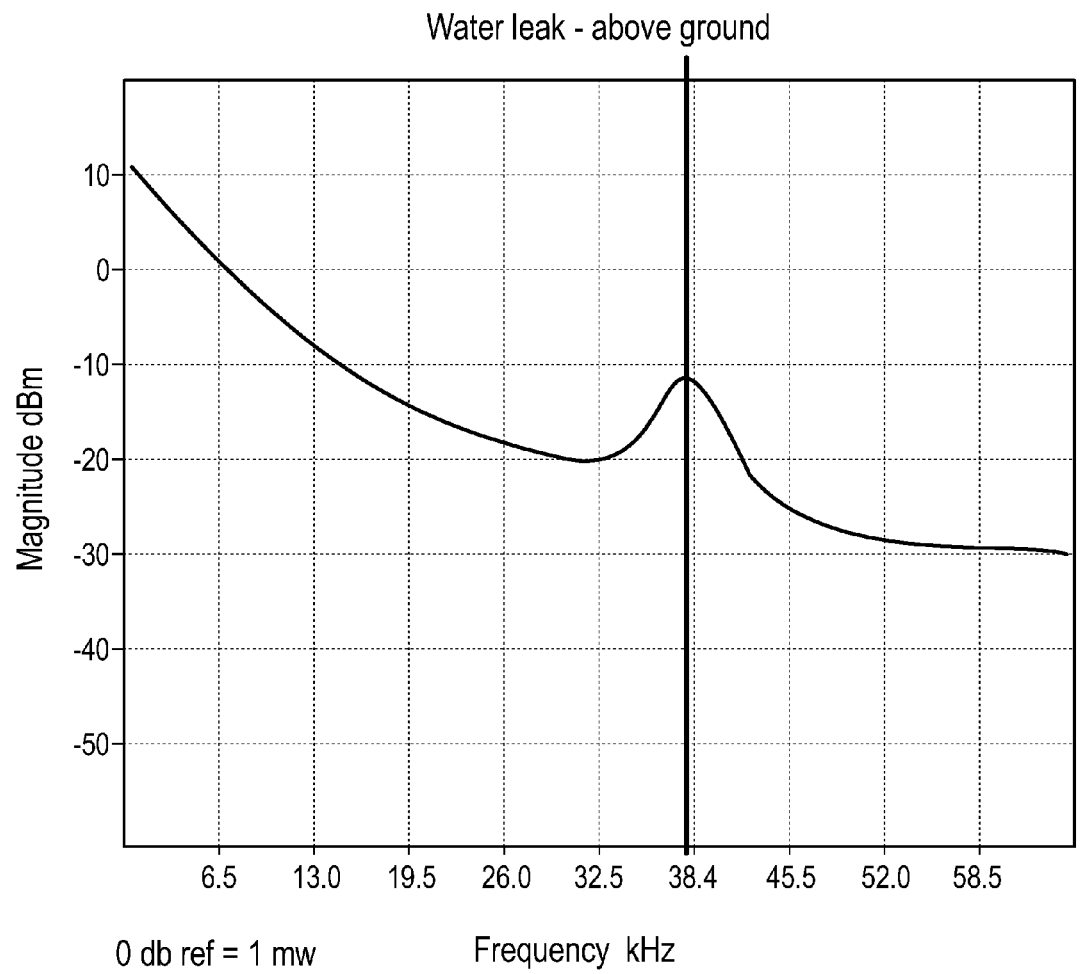
Figure 21:
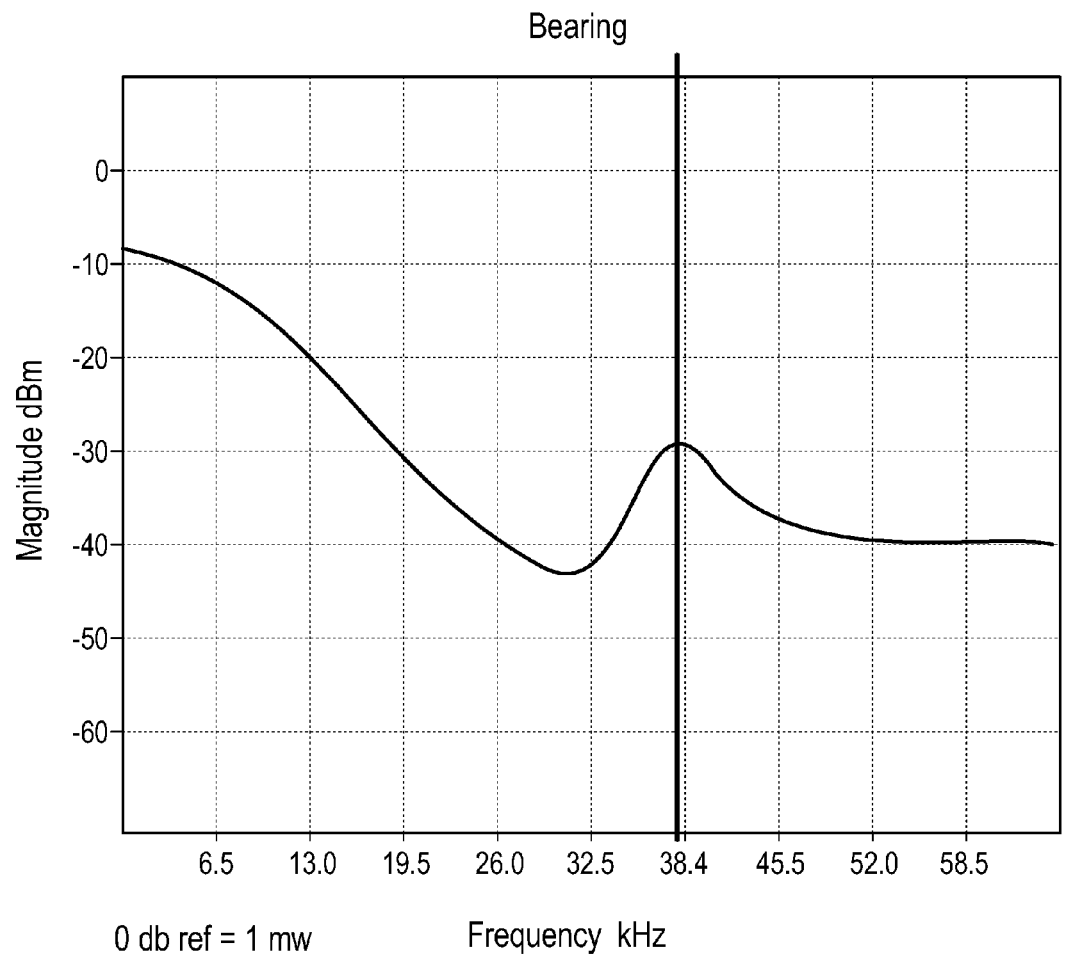
Figure 22:
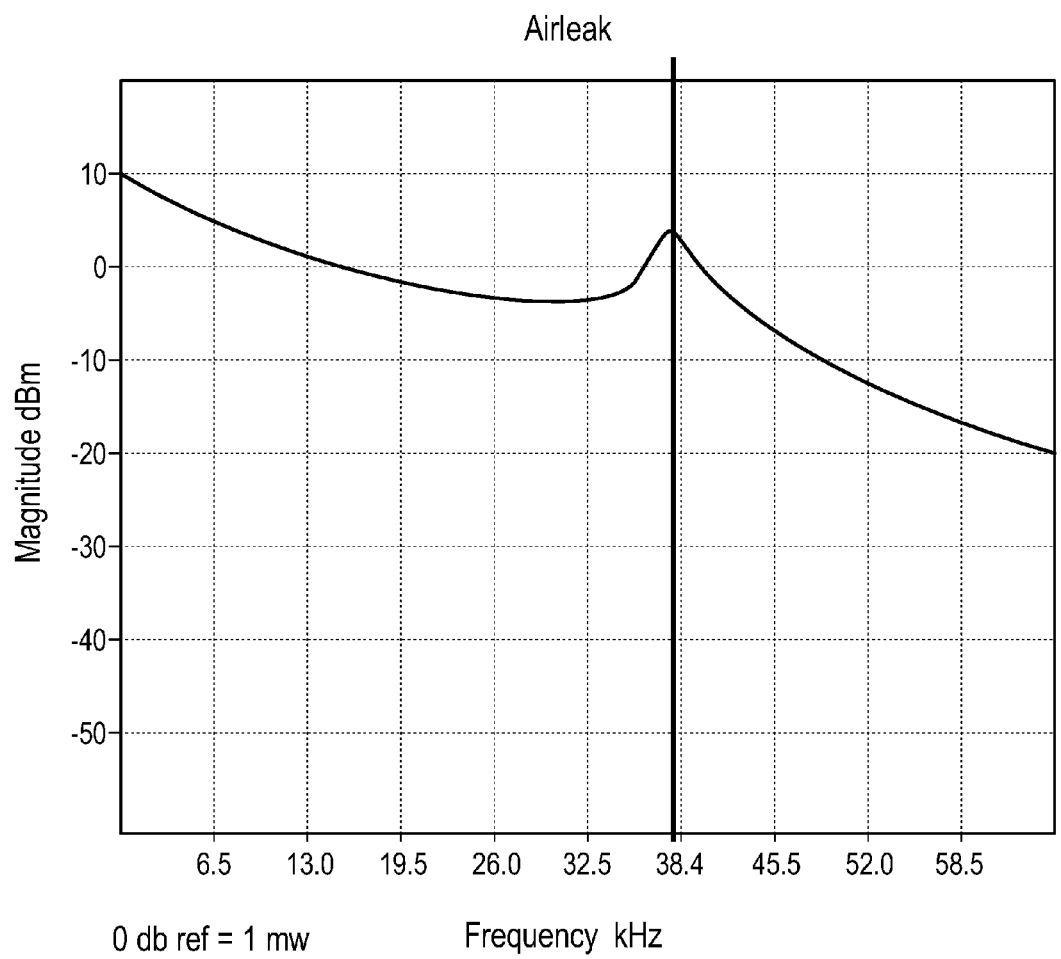

Referring now to FIG. 18, an exemplary data collection process may be described as may typically be performed by a technician, customer or partner entity in accordance with the present disclosure. In an embodiment, many steps in the process of FIG. 18 may typically be performed using a sound detection device 1600 and associated control circuitry as represented in FIGS. 16-17 and further described below. However, alternative configurations of a sound detection device and control circuitry may be contemplated in view of this description as a whole as being within the scope of the present invention.

A party such as a program partner technician initiates the process by turning on a sound detection device (step 1801) and scanning a pre-arranged barcode (or alternative machine-readable component) for a piece of equipment or an associated inspection point (step 1802). Having sufficiently identified the equipment or inspection point, the technician positions a sound cup associated with the sound detection device in accordance with the type and location of the equipment or inspection point (step 1803). For example, the positioning of the sound cup may typically be dependent on the shape, size, location and/or positioning of the equipment itself.

The technician may then implement a wireless headset and the sound detection device with sound cup to listen for primary sounds emitted from the equipment (step 1804), and may interface with the sound detection device to reduce the amount, degree and/or effects of secondary noise emitted from the equipment or otherwise associated with the received sound energy (step 1805). The technician may then initiate and terminate a sound measurement process (step 1806), via for example a first and a second user input with respect to a manual actuator such as a button on the sound detection device, and then replay, monitor or otherwise review the sound input to verify a proper sound recording (step 1807).

The user interface of the sound detection device and appropriate programming may enable the technician to generate a sound file associated with the specific measurement (step 1808), and further to generate a data file defining for example the equipment, location, time or any other relevant information with respect to that sound measurement (step 1809). In embodiments, the data file may be an independent data file to be uploaded alongside the sound file. Alternatively, the data file may be a digital object or container within which the sound file is embedded, and further including for example metadata identifying the equipment, location, time or any other relevant information with respect to that sound measurement.

The technician may continue by repeating steps 1802-1809 for each inspection point associated with a particular piece of equipment, for each piece of equipment in a particular location, etc. (step 1810), thereby generating a like plurality of sound files, data files, etc. The technician may then log on to a mobile application via a mobile computing device such as a smart phone (step 1811), which enables the technician to subsequently upload the sound files, data files, etc., to the remote hosted server for further analysis (step 1812). Upon validating that the upload is complete (step 1813), the technician may log off (step 1814) and potentially continue to another location, customer, etc., wherein the process may be repeated.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

The term "coupled" means at least either a direct electrical connection between the connected items or an indirect connection through one or more passive or active intermediary devices.

Certain illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

Certain steps of a method, process, or algorithm described in connection with the embodiments disclosed herein, may unless expressly disclosed as being performed manually by a user be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable medium known in the art. An exemplary computer-readable medium can be coupled to the processor such that the processor can read information from, and write information to, the memory/storage medium. In the alternative, the medium can be integral to the processor. The processor and the medium can reside in an ASIC. The ASIC can reside in a user terminal. In the alternative, the processor and the medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The previous detailed description has been provided for the purposes of illustration and description. Thus, although there have been described particular embodiments of the present invention, it is not intended that such references be construed as limitations upon the scope of this invention except as set forth in the following claims.

What is claimed is:

1. A handheld ultrasound detection apparatus, comprising:
a housing comprising a display device;
a flexible tube having a first end attached to the housing, the flexible tube housing an ultrasound receiver for receiving ultrasound energy and converting the ultrasound energy into an electronic signal;
a gain/active filter comprising a plurality of amplifiers each having an associated gain range; and
logic configured to
receive the electronic signal from the ultrasound receiver,
based on a size of the electronic signal, to direct the electronic signal along a linear scale through one or more of the plurality of amplifiers and apply an appropriate gain to the signal,
generate a percentage value corresponding to the gain and with respect to the linear scale, and
enable user selection of a manual mode or an automatic mode of operation,
wherein during the manual mode of operation the logic generates display data corresponding to a particular gain range and a percentage value from 0-100% with respect to the particular gain range, and
wherein during the automatic mode of operation the logic generates display data corresponding to a percentage value from 0-(x times 100)% with respect to a collective gain range defined by the plurality (x) of amplifiers.

2. The handheld ultrasound detection apparatus of claim 1, the plurality of amplifiers comprising four amplifiers defining a collective gain range, wherein a percentage value is generated in the automatic mode of operation along a linear scale from 0-400%.

3. The handheld ultrasound detection apparatus of claim 1, further comprising a sound cup coupled to a second end of the flexible tube and configured to provide sounds received therein to the ultrasound receiver.

4. The handheld ultrasound detection apparatus of claim 1, further comprising a base located on a front end of the housing;
a laser located adjacent to the base; and
a detector located adjacent to the laser,
wherein the logic is further configured to calculate a distance between the housing and an object at which the laser is pointed based upon light transmitted by the laser, reflected by the object, and received by the detector.

5. The handheld ultrasound detection apparatus of claim 4, wherein the logic is further configured to generate display data corresponding to the calculated distance.

6. The handheld ultrasound detection apparatus of claim 1, wherein the base comprises a threaded opening, and the flexible tube comprises a threaded protrusion that is threadedly coupled to the threaded opening of the base.

7. The handheld ultrasound detection apparatus of claim 1, wherein the flexible tube is welded to the base.

8. A handheld ultrasound detection apparatus, comprising:
a first housing comprising a display device;
a flexible tube attached at a first end to the first housing;
an ultrasound receiver disposed within the flexible tube, said receiver for receiving ultrasound energy and converting the ultrasound energy into an electronic signal;
a second housing functionally linked to the first housing and further comprising a plurality of amplifiers each having an associated gain range, and logic configured to
receive the electronic signal from the ultrasound receiver,
based on a size of the electronic signal, to direct the electronic signal along a linear scale through one or more of the plurality of amplifiers and apply an appropriate gain to the signal,
generate a percentage value corresponding to the gain and with respect to the linear scale, and
enable user selection of a manual mode or an automatic mode of operation,
wherein during the manual mode of operation the logic generates display data corresponding to a particular gain range and a percentage value from 0-100% with respect to the particular gain range,
wherein during the automatic mode of operation the logic generates display data corresponding to a percentage value from 0-(x times 100)% with respect to a collective gain range defined by the plurality (x) of amplifiers.

9. The handheld ultrasound detection apparatus of claim 8, the plurality of amplifiers comprising four amplifiers defining a collective gain range, wherein a percentage value is generated in the automatic mode of operation along a linear scale from 0-400%.

10. The handheld ultrasound detection apparatus of claim 8, further comprising a sound cup coupled to a second end of the flexible tube and configured to provide sounds received therein to the ultrasound receiver.

11. The handheld ultrasound detection apparatus of claim 8, further comprising
a base located on a front end of the first housing;
a laser located adjacent to the base; and
a detector located adjacent to the laser,
wherein the logic is further configured to calculate a distance between the first housing and an object at which the laser is pointed based upon light transmitted by the laser, reflected by the object, and received by the detector.

12. The handheld ultrasound detection apparatus of claim 11, wherein the logic is further configured to generate display data corresponding with the calculated distance.

13. The handheld ultrasound detection apparatus of claim 8, wherein the base comprises a threaded opening, and the flexible tube comprises a threaded protrusion that is threadedly coupled to the threaded opening of the base.

14. The handheld ultrasound detection apparatus of claim 8, wherein the flexible tube is welded to the base.

15. An ultrasound detection system comprising:
a first and a second handheld ultrasound detection apparatus, each apparatus further comprising
a housing comprising a display device;
a flexible tube having a first end attached to the housing, the flexible tube housing an ultrasound receiver for receiving ultrasound energy and converting the ultrasound energy into an electronic signal according to a calibration factor;
a gain/active filter comprising a plurality of amplifiers each having an associated gain range; and
logic configured to
receive the electronic signal from the ultrasound receiver,
based on a size of the electronic signal, to direct the electronic signal along a linear scale through one or more of the plurality of amplifiers and apply an appropriate gain to the signal,
generate a percentage value corresponding to the gain and with respect to the linear scale, and
enable user selection of a manual mode or an automatic mode of operation,
wherein during the manual mode of operation the logic generates display data corresponding to a particular gain range and a percentage value from 0-100% with respect to the particular gain range,
wherein during the automatic mode of operation the logic generates display data corresponding to a percentage value from 0-(x times 100)% with respect to a collective gain range defined by the plurality (x) of amplifiers, and
wherein each of the first and second apparatus comprises a common calibration factor and disables user adjustment of the calibration factor.

16. The system of claim 15, the plurality of amplifiers for each apparatus comprising four amplifiers defining a collective gain range, wherein a percentage value is generated in the automatic mode of operation along a linear scale from 0-400%.

17. The system of claim 15, each apparatus further comprising a sound cup coupled to a second end of the flexible tube and configured to provide sounds received therein to the ultrasound receiver.

* * * * *